(12) United States Patent
Harris, III et al.

(10) Patent No.: US 7,229,984 B2
(45) Date of Patent: Jun. 12, 2007

(54) DIBENZOXAZEPINONE DERIVATIVES AND USES THEREOF

(75) Inventors: Ralph New Harris, III, Redwood City, CA (US); James M. Kress, Sanford, NC (US); David Bruce Repke, Milpitas, CA (US); Russell Stephen Stabler, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/298,245

(22) Filed: Dec. 9, 2005

(65) Prior Publication Data

US 2006/0154914 A1    Jul. 13, 2006

Related U.S. Application Data

(60) Provisional application No. 60/634,723, filed on Dec. 9, 2004.

(51) Int. Cl.
| | |
|---|---|
| C07D 267/02 | (2006.01) |
| C07D 281/02 | (2006.01) |
| C07D 243/10 | (2006.01) |
| C07D 498/00 | (2006.01) |
| A61K 31/55 | (2006.01) |

(52) U.S. Cl. .................. 514/211.04; 514/211.11; 514/220; 540/488; 540/495; 540/547

(58) Field of Classification Search .......... 540/488, 540/495, 547; 514/211.04, 211.11, 220
See application file for complete search history.

(56) References Cited

OTHER PUBLICATIONS

Klunder, Janice M., *Novel Non-Nucleoside Inhibitors of HIV-1 Reverse Transcriptase. 2. Tricyclic Pyridobenzoxazepinones and Dibenzoxazepinones*, J. Med. Chem., 1992, pp. 1887-1897, vol. 35(10).

*Primary Examiner*—Bruck Kifle
(74) *Attorney, Agent, or Firm*—Robert C. Hall

(57) ABSTRACT

Compounds of the Formula I:

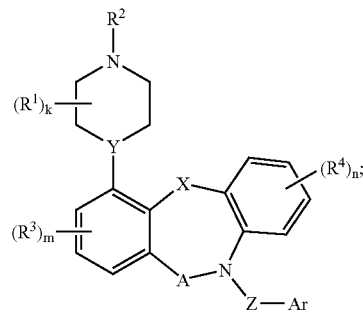

wherein m, n, k, A, X, Y, Z, Ar, $R^1$, $R^2$, $R^3$, and $R^4$ are as defined herein. The compounds are useful as 5-HT6 receptor antagonists. Also provided are compositions comprising, methods of using, and methods of making the subject compounds.

24 Claims, No Drawings

DIBENZOXAZEPINONE DERIVATIVES AND USES THEREOF

CROSS-REFERENCE

This application claims the benefit of priority of U.S. Provisional Patent Application Ser. No. 60/634,723 filed Dec. 9, 2004, the disclosure of which is incorporated herein by reference in its entirety.

FIELD OF THE INVENTION

This invention relates to dibenzoxazepinone compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8.

While some 5-HT6 and 5-HT2A modulators have been disclosed, there continues to be a need for compounds that are useful for modulating the 5-HT6 receptor, the 5-HT2A receptor, or both.

SUMMARY

The present invention provides compounds of the Formula I:

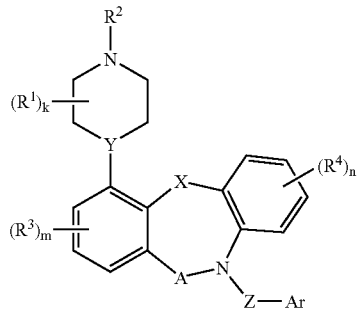

wherein
A is C(=O) or CH$_2$;
X is —O—, —S(O)$_q$—, or —NR$^8$—;
Y is —N— or —CH—;
Z is —(CR$^6$R$^7$)$_r$—, or —S(O)$_t$—;
Ar is optionally substituted aryl or optionally substituted heteroaryl each R$^1$ is independently hydrogen or alkyl;
each of R$^2$, R$^6$, R$^7$ and R$^8$ is independently hydrogen or alkyl;
each of R$^3$ and R$^4$ is independently halo, alkyl, haloalkyl, heteroalkyl, alkoxy, cyano, —S(O)$_s$—R$^c$, —C(=O)—NR$^c$R$^d$, —SO$_2$—NR$^c$R$^d$, —N(R$^c$)—C(=O)—R$^d$, or —C(=O)—R$^c$;
each of R$^c$ and R$^d$ is independently hydrogen or alkyl;
each of m and n is independently an integer from 0 to 3;
r is an integer from 1 to 3; and
each of k, q, s, and t is independently an integer from 0 to 2.

It should be understood that the scope of the present invention encompasses not only the various isomers that may exist but also the various mixture of isomers that may be formed. Furthermore, the scope of the present invention also encompasses solvates and salts of compounds of formula II.

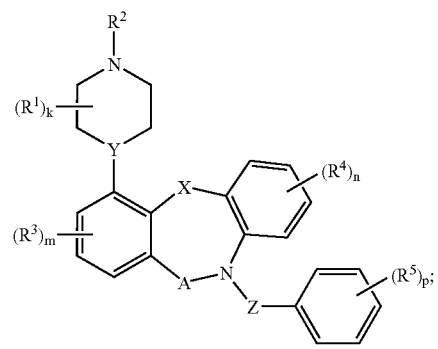

or a pharmaceutically acceptable salt, solvate or prodrug thereof, wherein
A is C(=O) or CH$_2$;
X is —O—, —S(O)$_q$—, or —NR$^8$—;
Y is —N— or —CH—;
Z is —(CR$^6$R$^7$)$_r$—, or —S(O)$_t$—;
each R$^1$ is independently hydrogen or alkyl;
each of R$^2$, R$^6$, R$^7$, R$^8$ is independently hydrogen or alkyl;
each of R$^3$, R$^4$, and R$^5$ is independently halo, alkyl, haloalkyl, heteroalkyl, alkoxy, cyano, —S(O)$_s$—R$^c$, —C(=O)—NR$^c$R$^d$, —SO$_2$—NR$^c$R$^d$, —N(R$^c$)—C(=O)—R$^d$, or —C(=O)R$^c$;
each of R$^c$ and R$^d$ is independently hydrogen or alkyl;
each of m, n, and p is independently an integer from 0 to 3;
r is an integer from 1 to 3; and
each of k, q, s, and t is independently an integer from 0 to 2.

The present invention also provides methods for preparing the aforementioned compounds. The subject methods may comprise, in certain embodiments, reacting an amino benzoxazepinone compound of the formula:

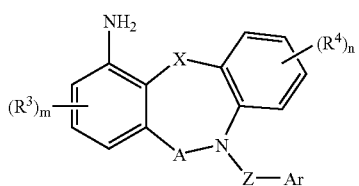

III with an amino compound of the formula:

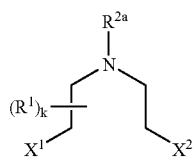

IV to yield a benzoxazepinone compound of the formula:

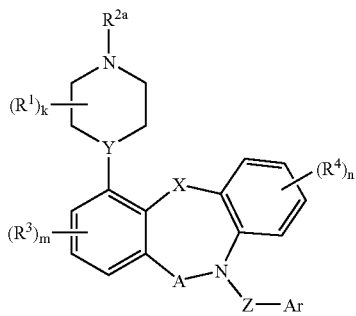

V wherein Ar, $R^1$, $R^3$, $R^4$, A, X, Y, Z, k, m and n are those defined herein; $R^{2a}$ is hydrogen, alkyl, or an amino-protecting group; and each of $X^1$ and $X^2$ is independently a leaving group.

In another embodiment, methods may comprise reacting a heterocyclyl benzoxazepinone compound of the formula:

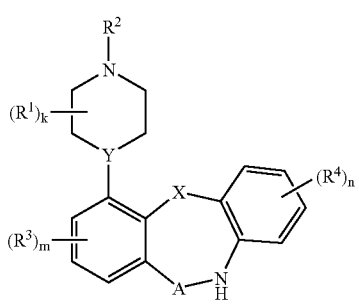

VI with an aryl compound of the formula:

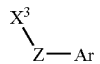

VII to produce a benzoxazepinone compound of the formula:

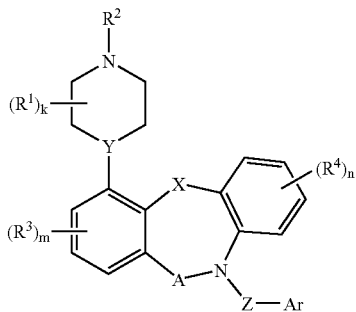

I wherein $X^3$ is a leaving group; and Ar, $R^1$, $R^2$, $R^3$, $R^4$, A, X, Y, Z, k, m, and n are those defined herein.

DETAILED DESCRIPTION OF THE INVENTION

The invention provides substituted benzoxazepinone compounds, associated compositions, methods for use as therapeutic agents, and methods of preparation thereof. One embodiment of the present invention provides heterocyclyl-substituted (e.g., piperazinyl-substituted) benzoxazepinone compounds and associated pharmaceutical compositions, and methods for using the same in the treatment of central nervous system (CNS) diseases and gastrointestinal tract disorders.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$–$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Cycloalkyl" means a saturated carbocyclic moiety consisting of mono- or bicyclic rings; Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphihyridinyl, pteridinyl, carbazolyl, azepinyl, diazepinyl, acridinyl and the like, including partially hydrogenated derivatives thereof.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Optionally substituted", when used in association with "aryl", or "heteroaryl" means an aryl, or heteroaryl that is optionally substituted independently with one or more, e.g., one to four substituents, preferably one or two substituents, selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R")_n$—COOR (where n is an integer from 0 to 5, R' and R" are independently hydrogen or alkyl, and R is hydrogen, alkyl, cycloalkyl, cycloalkylalkyl, phenyl or phenylalkyl), —$(CR'R")_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl), —$S(O)_s$—$R^c$ (where s is 0, 1 or 2; and $R^c$ is hydrogen or alkyl), —$SO^2$—$NR^cR^d$ (where each of $R^c$ and $R^d$ is independently hydrogen or alkyl), and —$N(R^c)$—C(=O)—$R^d$ (where each of $R^c$ and $R^d$ is independently hydrogen or alkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state , i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative quinoline compounds described herein is shown by the formula:

Chemical structures shown herein were prepared using ISIS™/Draw version 2.5. Any open valency appearing on a carbon, oxygen or nitrogen atom in the structures herein indicates the presence of a hydrogen.

Compounds of the Invention

One aspect of the present invention provides compounds of the formula I:

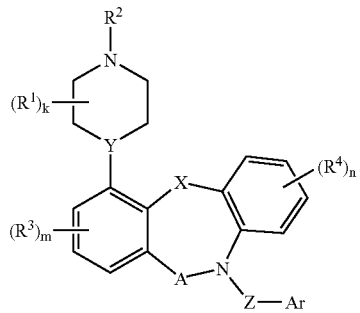

I wherein
A is C(=O) or CH$_2$;
X is —O—, —S(O)$_q$—, or —NR$^8$—;
Y is —N— or —CH—;
Z is —(CR$^6$R$^7$)— or —S(O)$_t$—;
Ar is optionally substituted aryl or optionally substituted heteroaryl each R$^1$ is independently hydrogen or alkyl;
each of R$^2$, R$^6$, R$^7$ and R$^8$ is independently hydrogen or alkyl;
each of R$^3$ and R$^4$ is independently halo, alkyl, haloalkyl, heteroalkyl, alkoxy, cyano, —S(O)$_s$—R$^c$, —C(=O)—NR$^c$R$^d$, —SO$_2$NR$^c$R$^d$, —N(R$^c$)—C(=O)—R$^d$, or —C(=O)—R$^c$;
each of R$^c$ and R$^d$ is independently hydrogen or alkyl;
each of m and n is independently an integer from 0 to 3;
r is an integer from 1 to 3; and
each of k, q, s, and t is independently an integer from 0 to 2.

It should be understood that the scope of the present invention encompasses not only the various isomers that may exist but also the various mixture of isomers that may be formed. Furthermore, the scope of the present invention also encompasses prodrugs, solvates and salts of compounds of formula I.

In some embodiments, A is C=O.
In other embodiments, A is —CH$_2$—. In these particular embodiments, preferably Z is —S(O)$_t$—, where t is as defined herein.
Yet in other embodiments, each of R$^3$ and R$^4$ is independently alkyl, alkoxy, halo, hydroxyl, cyano, haloalkyl, or —S(O)$_u$-alkyl, and wherein u is an integer from 0 to 2.
In some embodiments, R$^3$ is halo.
Still in other embodiments, R$^4$ is halo, alkyl, or —S(O)$_u$-alkyl, where u is as defined herein.
In certain embodiments Ar is optionally substituted aryl. In such embodiments, Ar is more preferably optionally substituted phenyl.
In some embodiments Ar is optionally substituted heteroaryl. Preferred heteroaryl include thienyl, pyridyl and indolyl, each of which may be optionally substituted. Exemplary heteroaryl include pyridin-3-yl, 2-chlorothien-5-yl and indol-3-yl.

In other embodiments, m is 0 or 1.
Yet still in other embodiments, n is 0 or 1.
Still in other embodiments, p is 0 or 1.
Yet in other embodiments, X is —S(O)$_q$—, where q is as defined herein.
In many embodiments, X is —O—.
In some embodiments, Y is —CH—.
In other embodiments, Y is —N—.
In certain embodiments, Z is —CR$^6$R$^7$)$_r$— or —S(O)$_t$—, where r, t, R$^6$, and R$^7$ are as defined herein. In one particular embodiment, Z is —(CR$^6$R$^7$)$_r$—, where r, R$^6$, and R$^7$ are as defined herein. Within this particular embodiment, preferably R$^6$ and R$^7$ are hydrogen.
Yet in other embodiments, k is 0.
In other embodiments, R$^2$ is hydrogen or alkyl. In specific embodiments, R$^2$ is hydrogen or methyl.

The compounds of the invention in many embodiments are more specifically of the formula II:

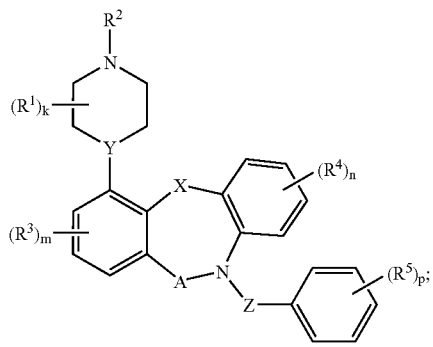

II wherein
A is C(=O) or CH$_2$;
X is —O—, —S(O)$_q$—, or —NR$^8$—;
Y is —N— or —CH—;
Z is —(CR$^6$R$^7$)$_r$—, or —S(O)$_t$—;
each R$^1$ is independently hydrogen or alkyl;
each of R$^2$, R$^6$, R$^7$, R$^8$ is independently hydrogen or alkyl;
each of R$^3$, R$^4$, and R$^5$ is independently halo, alkyl, haloalkyl, heteroalkyl, alkoxy, cyano, —S(O)$_s$—R$^c$, —C(=O)—NR$^c$R$^d$, —SO$_2$—NR$^c$R$^d$, —N(R$^c$)—C(=O)—R$^d$, or —C(=O)—R$^c$;
each of R$^c$ and R$^d$ is independently hydrogen or alkyl;
each of m, n, and p is independently an integer from 0 to 3;
r is an integer from 1 to 3; and
each of k, q, s, and t is independently an integer from 0 to 2.

It should be understood that the scope of the present invention encompasses not only the various isomers which may exist but also the various mixture of isomers which may be formed. Furthermore, the scope of the present invention also encompasses prodrugs, solvates and salts of compounds of formula II.

In some embodiments, A is C=O.
In other embodiments, A is —CH$_2$—. In this particular embodiment, preferably Z is —S(O)$_t$—, where t is as defined herein.
Yet in other embodiments, each of R$^3$, R$^4$, and R$^5$ is independently alkyl, alkoxy, halo, hydroxyl, cyano, haloalkyl, or —S(O)$_u$-alkyl, and wherein u is an integer from 0 to 2.

In some embodiments, $R^3$ is halo.

Still in other embodiments, $R^4$ is halo, alkyl, or —S(O)$_u$-alkyl, where u is as defined herein.

Yet in other embodiments, $R^5$ is halo, alkyl, alkoxy, haloalkyl, cyano, hydroxyl, or —S(O)$_u$-alkyl, where u is as defined herein.

In other embodiments, m is 0 or 1.

Yet still in other embodiments, n is 0 or 1.

Still in other embodiments, p is 0 or 1.

Yet in other embodiments, X is —S(O)$_q$—, where q is as defined herein.

In many embodiments, X is —O—.

In some embodiments, Y is —CH—.

In other embodiments, Y is —N—.

In certain embodiments, Z is —CR$^6$R$^7$)$_r$— or —S(O)$_t$—, where r, t, R$^6$, and R$^7$ are as defined herein. In one particular embodiment, Z is —CR$^6$R$^7$)$_r$—, where r, R$^6$, and R$^7$ are as defined herein. Within this particular embodiment, preferably R$^6$ and R$^7$ are hydrogen.

Yet in other embodiments, k is 0.

In other embodiments, $R^2$ is hydrogen or alkyl. In specific embodiments, $R^2$ is hydrogen or methyl.

It should be appreciated that combinations of the different groups described herein may form other embodiments. In this manner, a variety of different compounds are embodied within the present invention.

Where any of $R^1$, $R^2$, $R^3$, $R^4$, $R^5$, $R^6$, $R^7$, $R^8$, $R^c$ and $R^d$ herein are alkyl or contain an alkyl moiety, such alkyl is preferably lower alkyl, i.e. $C_1$–$C_6$alkyl, and more preferably $C_1$–$C_4$alkyl.

Representative compounds in accordance with the invention are shown in Table 1 together with melting point or mass spectrum M+H, and the experimental examples (described below) associated with each compound.

TABLE 1

| # | Structure | Name | MP (° C.) or M + H |
|---|---|---|---|
| 1 | 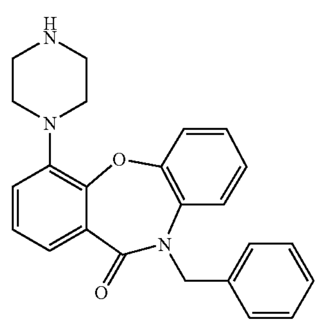 | 10-Benzyl-4-piperazin-1-yl-10H-dibenzo[b,f][1,4]oxazepin-11-one | 198–199° C. (HCl salt) |
| 2 | 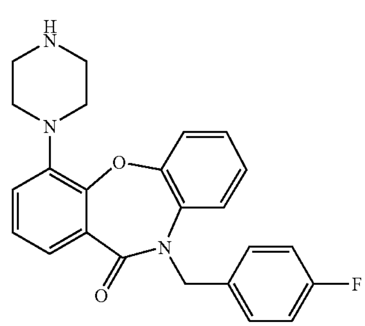 | 10-(4-Fluoro-benzyl)-4-piperazin-1-yl-10H-dibenzo[b,f][1,4]oxazepin-11-one | 214–216° C. (HCl salt) |
| 3 | 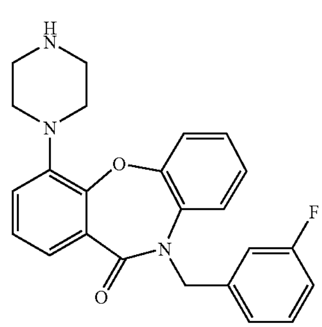 | 10-(3-Fluoro-benzyl)-4-piperazin-1-yl-10H-dibenzo[b,f][1,4]oxazepin-11-one | 191–192° C. (HCl salt) |

TABLE 1-continued

| # | Structure | Name | MP (° C.) or M + H |
|---|---|---|---|
| 4 | 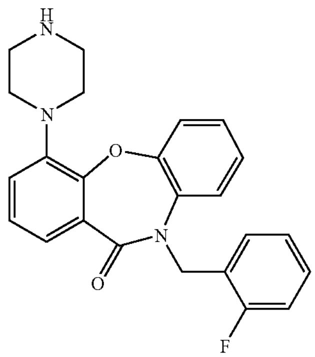 | 10-(2-Fluoro-bvenzyl)-4-piperazin-1-yl-10H-dibenzo[b,f][1,4]oxazepin-11-one | 404 (M + 1) |
| 5 | 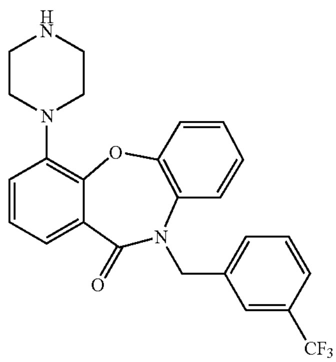 | 4-Piperzazin-1-yl-10-(3-trifluoromethyl-benzyl)-10H-dibenzo[b,f][1,4]oxazepin-11-one | 454 (M + 1) |
| 6 | 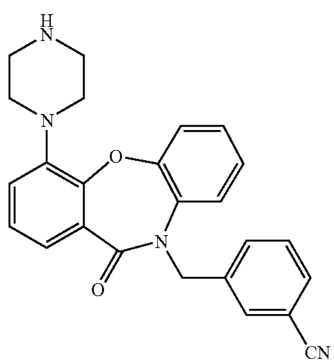 | 3-(11-Oxo-4-piperazin-1-yl-11H-dibenzo[b,f][1,4]oxazepin-10-ylmethyl)-benzonitrile | 192–194° C. (HCl salt) |
| 7 | 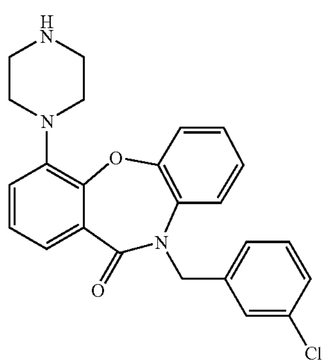 | 10-(3-Chloro-benzyl)-4-piperazin-1-yl-10H-dibenzo[b,f][1,4]oxazepin-11-one | 420, 422 (M + 1) |

TABLE 1-continued

| # | Structure | Name | MP (° C.) or M + H |
|---|---|---|---|
| 8 | 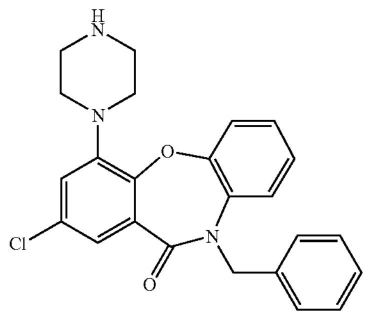 | 10-Benzyl-2-chloro-4-piperazin-1-yl-10H-dibenzo[b,f][1,4]oxazepin-11-one | 196–197° C. (HCl salt) |
| 9 | 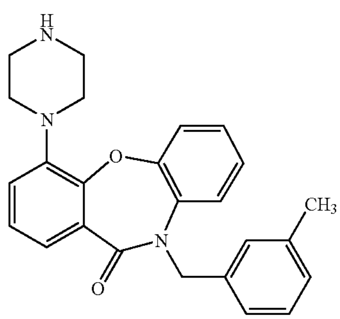 | 10-(3-Methyl-benzyl)-4-piperazin-1-yl-10H-dibenzo[b,f][1,4]oxazepin-11-one | 400 (M + 1) |
| 10 | 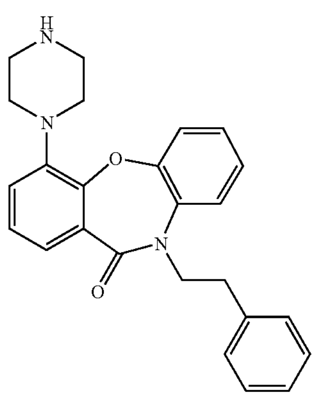 | 10-Phnethyl-4-piperazin-1-yl-10H-dibenzo[b,f][1,4]oxazepin-11-one, hydrochloride | 400 (M + 1) |
| 11 | 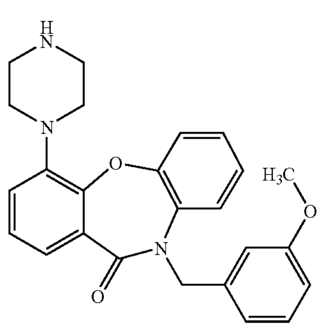 | 10-(3-Methoxy-benzyl)-4-piperzazin-1-yl-10H-dibenzo[b,f][1,4]oxazepin-11-one | 416 (M + 1) |

TABLE 1-continued

| # | Structure | Name | MP (° C.) or M + H |
|---|---|---|---|
| 12 | 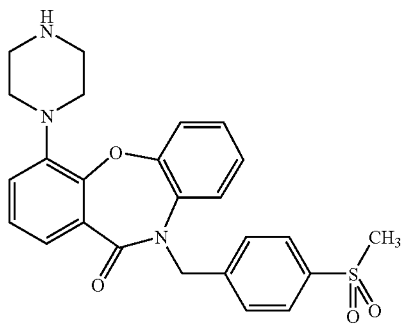 | 10-(4-Methanesulfonyl-benzyl)-4-piperazin-1-yl-10H-dibenzo[b,f][1,4]oxaezpin-11-one | 464 (M + 1) |
| 13 | 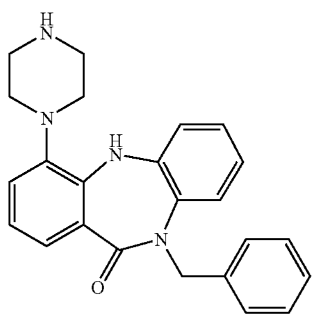 | 10-Benzyl-4-piperazin-1-yl-5,10-dihydro-dibenzo[b,e][1,4]diazepin-11-one | 322–323° C. (HCl salt) |
| 14 | 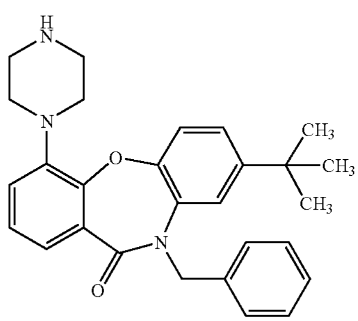 | 10-Benzyl-8-tert-butyl-4-piperazin-1-yl-10H-dibenzo[b,f][1,4]oxazepin-11-one | 292–293° C. (HCl salt) |
| 15 | 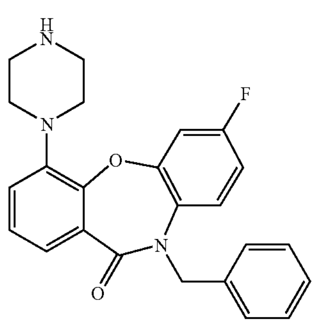 | 10-Benzyl-7-fluoro-4-piperazin-1-yl-10H-dibenzo[b,f][1,4]oxazepin-11-one | 404 (M + 1) |

TABLE 1-continued

| # | Structure | Name | MP (° C.) or M + H |
|---|---|---|---|
| 16 | 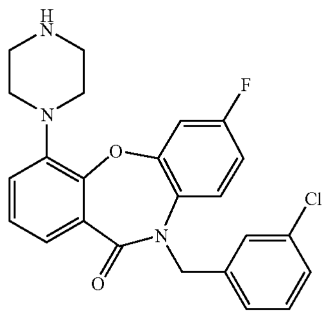 | 10-(3-Chloro-benzyl)-7-fluoro-4-piperazin-1-yl-10H-dibenzo[b,f][1,4]oxazepin-11-one | 483 (M + 1) |
| 17 | 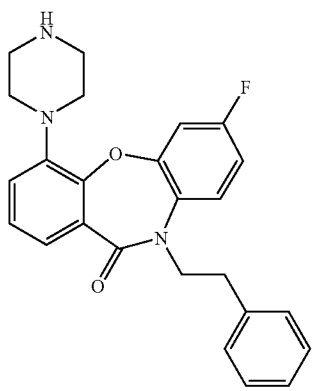 | 7-Fluoro-10-phenethyl-4-piperazin-1-yl-10H-dibenzo[b,f][1,4]oxazepin-11-one, hydrochloride | 418 (M + 1) |
| 18 | 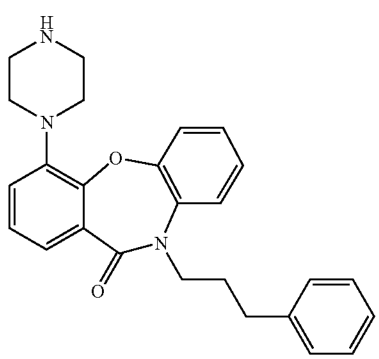 | 10-(3-Phenyl-propyl)-4-piperazin-1-yl-10H-dibenzo[b,f][1,4]oxazepin-11-one, hydrochloride | 415 (M + 1) |
| 19 | 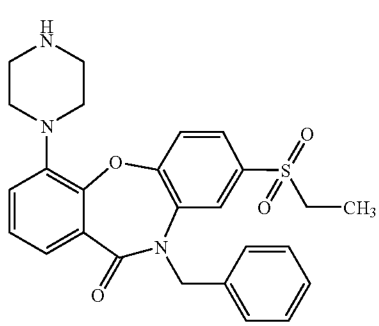 | 10-Benzyl-8-ethanesulfonyl-4-piperazin-1-yl-10H-dibenzo[b,f][1,4]oxazepin-11-one | 184–185° C. (HCl salt) |

TABLE 1-continued

| # | Structure | Name | MP (° C.) or M + H |
|---|---|---|---|
| 20 | 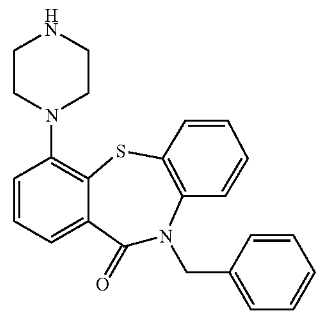 | 10-Benzyl-4-piperazin-1-yl-10H-dibenzo[b,f][1,4]thiazepin-11-one | 301–302° C. (HCl salt) |
| 21 | 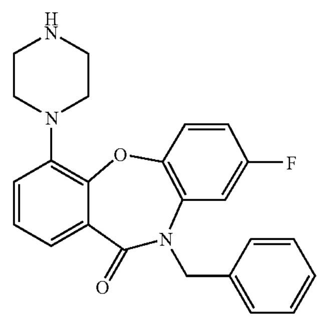 | 10-Benzyl-8-fluoro-4-piperazin-1-yl-10H-dibenzo[b,f][1,4]oxazepin-11-one | 404 (M + 1) |
| 22 | 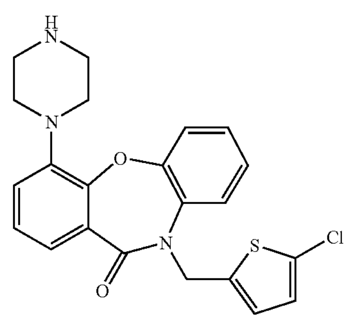 | 10-(5-Chloro-thiophen-2-ylmethyl)-4-piperazin-1-yl-10H-dibenzo[b,f][1,4]-oxazepin-11-one, hydrochloride | 427 (M + 1) |
| 23 | 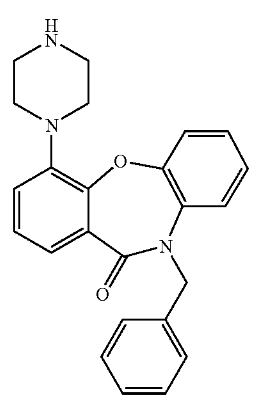 | 10-Benzyl-9-fluoro-4-piperazin-1-yl-10H-dibenzo[b,f][1,4]oxazepin-11-one | 178–180° C. (HCl salt) |

TABLE 1-continued

| # | Structure | Name | MP (° C.) or M + H |
|---|---|---|---|
| 24 | 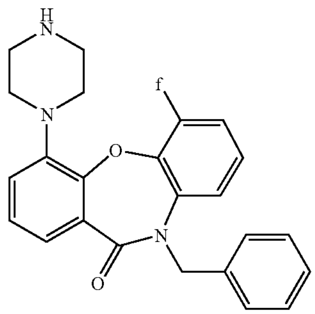 | 10-Benzyl-6-fluoro-4-piperazin-1-yl-10H-dibenzo[b,f][1,4]oxazepin-11-one | 404 (M + 1) |
| 25 | 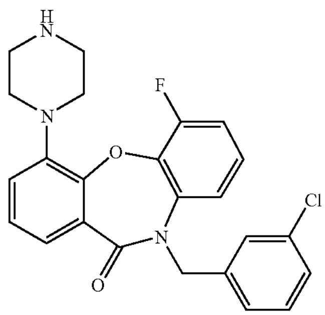 | 10-(3-Chloro-benzyl)-6-fluoro-4-piperazin-1-yl-10H-dibenzo[b,f][1,4]oxazepin-11-one | 438, 440 (M + 1) |
| 26 | 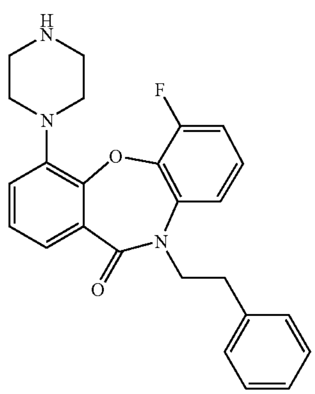 | 6-Fluoro-10-phenethyl-4-piperazin-1-yl-10H-dibenzo[b,f][1,4]oxazepin-11-one, hydrochloride | 418 (M + 1) |
| 27 | 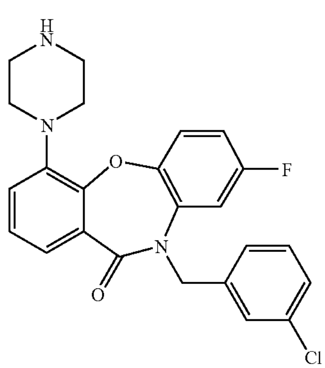 | 10-(3-Chloro-benzyl)-8-fluoro-4-piperazin-1-yl-10H-dibenzo[b,f][1,4]oxazepin-11-one | 438, 440 (M + 1) |

TABLE 1-continued

| # | Structure | Name | MP (° C.) or M + H |
|---|---|---|---|
| 28 | 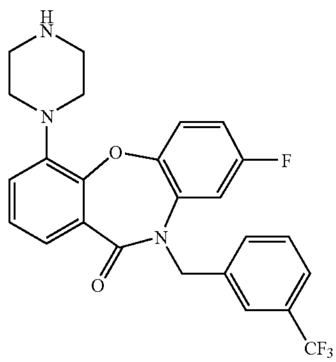 | 8-Fluoro-4-piperazin-1-yl-10-(3-trifluoromethyl-benzyl)-10H-dibenzo[b,f][1,4]oxazepin-11-one | 472 (M + 1) |
| 29 | 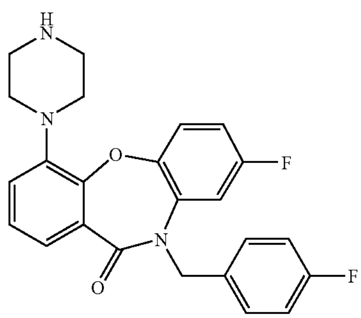 | 8-Fluoreo-10-(4-fluoro-benzyl)-4-piperazin-1-yl-10H-dibenzo[b,f][1,4]oxazepin-11-one | 422 (M + 1) |
| 30 | 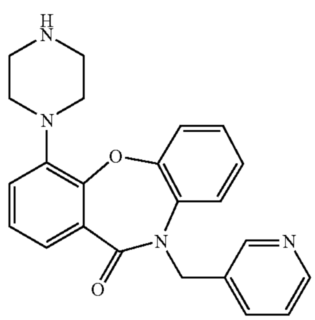 | 4-Piperazin-1-yl-10-pyridin-3-ylmethyl-10H-dibenzo[b,f][1,4]oxazepin-11-one | 387 (M + 1) |
| 31 | 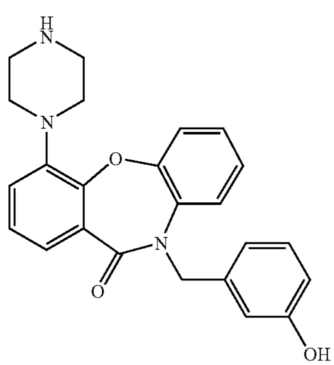 | 10-(3-Hydroxy-benzyl)-4-piperazin-1-yl-10H-dibenzo]b,f][1,4]oxazepin-11-one | 402 (M + 1) |

TABLE 1-continued

| # | Structure | Name | MP (° C.) or M + H |
|---|---|---|---|
| 32 | 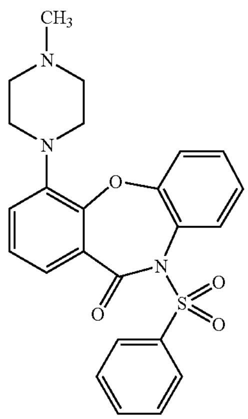 | 10-Benzenesulfonyl-4-(4-methyl-piperazin-1-yl)-10,11-dihydro-dibenzo[b,f][1,4]-oxazepin | 242–243° C. |
| 33 | 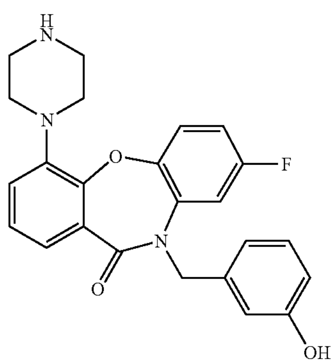 | 8-Fluoro-10-(3-hydroxy-benzyl)-4-piperazin-1-yl-10H-dibenzo[b,f][1,4]oxazepin-11-one | 420 (M + 1) |
| 34 | 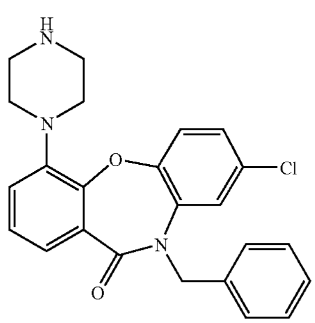 | 10-Benzyl-8-chloro-4-piperazin-1-yl-10H-dibenzo[b,f][1,4]oxazepin-11-one | 420, 422 (M + 1) |
| 35 | 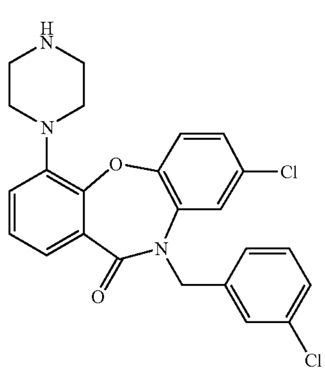 | 8-Chloro-10-(3-chloro-benzyl)-4-piperazin-1-yl-10H-dibenzo[b,f][1,4]oxazepin-11-one | 454, 456 (M + 1) |

TABLE 1-continued

| # | Structure | Name | MP (° C.) or M + H |
|---|---|---|---|
| 36 | 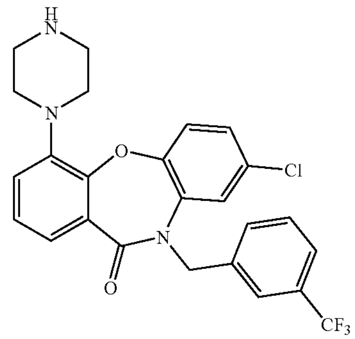 | 8-Chloro-4-piperazin-1-yl-10-(3-trifluoromethyl-benzyl)-10H-dibenzo[b,f][1,4]oxazepin-11-one | 488, 490 (M + 1) |
| 37 | 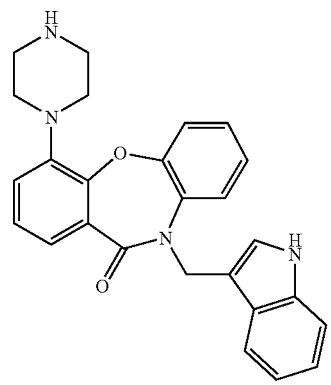 | 10-(1H-Indol-3-ylmethyl)-4-piperazin-1-yl-10H-dibenzo[b,f][1,4]oxazepin-11-one | 426 (M + 1) |
| 38 | 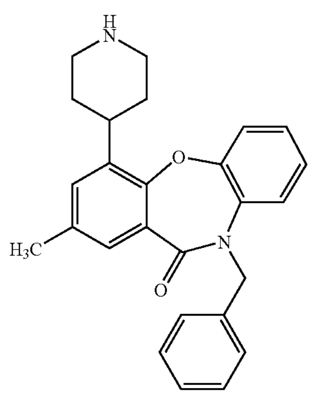 | 10-Benzyl-2-methyl-4-piperidin-4-yl-10H-dibenzo[b,f][1,4]oxazepin-11-,one, hydrochloride | 400 (M + 1) |

Another aspect of the invention provides a composition comprising a therapeutically effective amount of at least one compound of Formula I and a pharmaceutically acceptable carrier.

Yet another aspect of the invention provides a method for treating a central nervous system (CNS) disease state in a subject comprising administering to the subject a therapeutically effective amount of a compound of Formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of Formula I.

Another aspect of the present invention provides a method for producing a compound of Formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 2004, Volumes 1–56. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates some of the synthetic procedures usable to prepare compounds of the invention. Numerous synthetic routes to benzoxazepinone are known and may be used in preparation of the subject compounds, and the procedure of Scheme A is only exemplary. Specific examples of the procedures of Scheme A are provided in the following Experimental section.

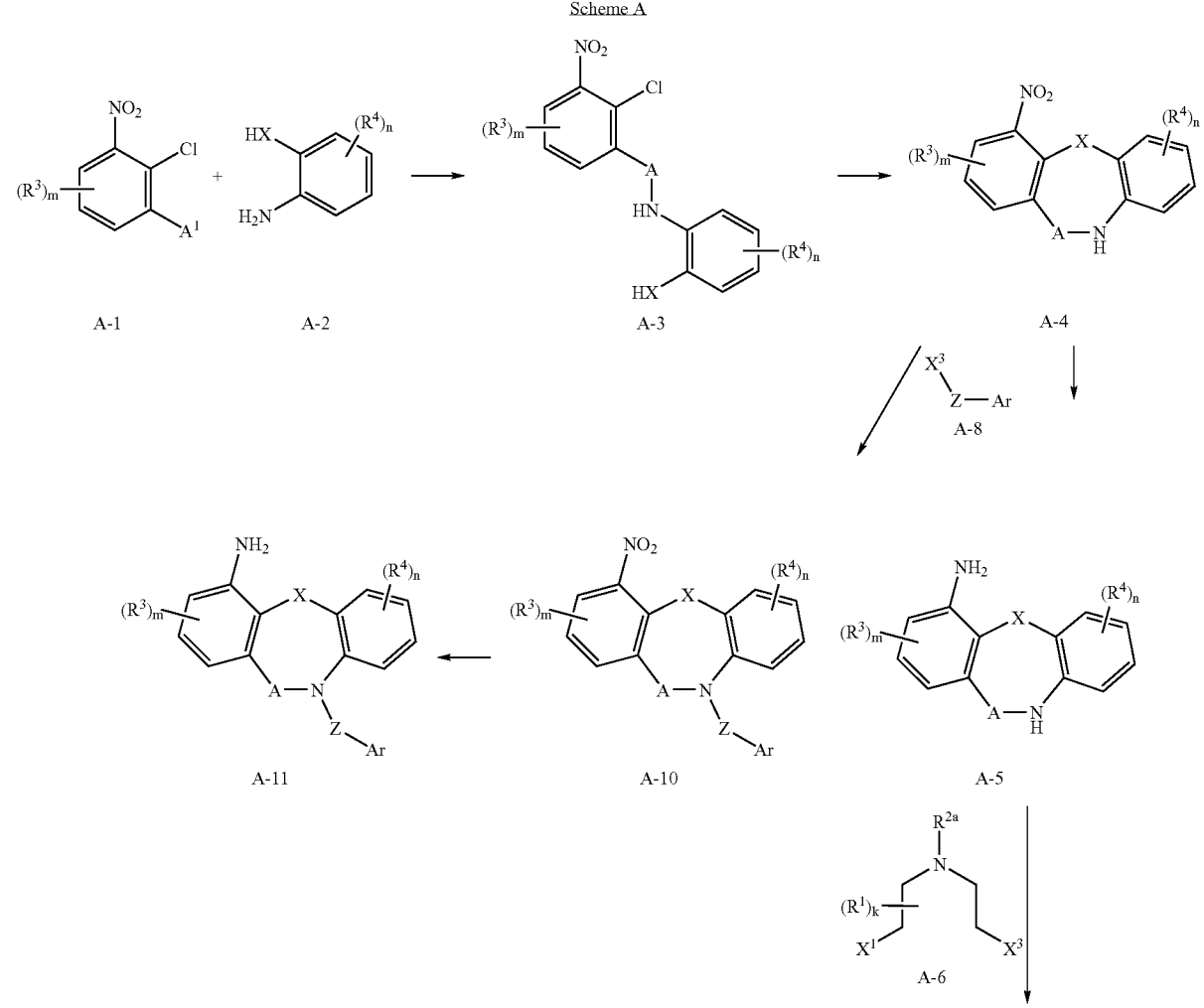

-continued

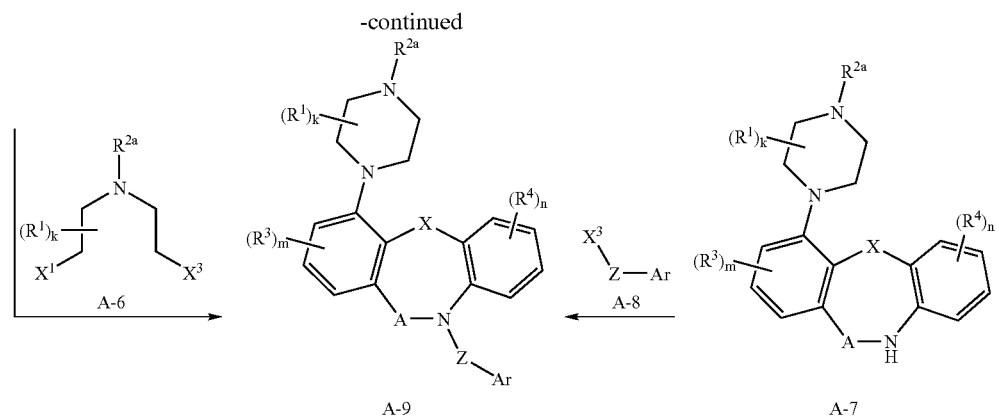

In Scheme A, a nitro-aryl compound A-1 is coupled with an aniline compound A-2 to provide a compound A-3. Typically, this coupling reaction is conducted under an inert aprotic solvent, such as methylene chloride, toluene or a mixture thereof. The substituent $A^1$ of the nitro-aryl compound A-1 is typically a carbonyl-containing group such as carboxylic acid, ester or an acyl halide. Alternatively, the substituent $A^1$ of the nitro-aryl compound A-1 may be a methylene-containing group with a leaving group that is capable of being displaced by the amino group of the aniline compound A-2.

Intramolecular cyclization of the compound A-3 then provides dibenzoxazepinone compound A-4 (where A is C=O). The intramolecular cyclization is generally conducted by heating the compound A-3 in the presence of a base, such as sodium hydroxide, and a polar solvent. Often the intramolecular cyclization reaction may be conducted in water.

The nitro group in compound A-4 is then reduced to an amino group to provide an aniline compound A-5. Suitable reaction conditions for reducing a nitro group to an amino group are well known to one skilled in the art. Typically, the reduction of the nitro group is achieved by hydrogenation reaction in the presence of a palladium catalyst and an acid, such as hydrochloric acid. When the substituent A is a carbonyl group (C=O), under certain reaction conditions one can simultaneously reduce the carbonyl group to a methylene group, if so desired.

Aniline compound A-5 is reacted with compound is treated with amino compound A-6 in a cyclization reaction that produces piperazinyl compound A-7. Alkylation of compound A-8 with compound A-8 then affords compound A-9. When $R^{2a}$ is an amino protecting group, it can be removed to provide a compound of Formula I where R is hydrogen.

Alternatively, compound A-4 can be treated directly with compound A-8 to affect an N-alkylation and provide compound A-10. The nitro group in compound A-10 may then be reduced to an amino group to provide the corresponding aniline compound A-11. Compound A-11 may then be treated with compound A-6 to afford compound A-9.

Numerous variations on the procedure of Scheme A are possible and will be apparent to those skilled in the art having the disclosure of the present invention. More specific details for producing compounds of Formula I are described in the Examples section below.

Utility

The compounds of the invention have selective affinity for 5-HT receptors, including the 5-HT$_6$ the 5-HT$_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. Additional compounds prepared using the experimental procedures below are shown in Table 1.

Example 1

This example illustrates a process for producing 2-chloro-N-(2-hydroxyphenyl)-3-nitro-benzamide.

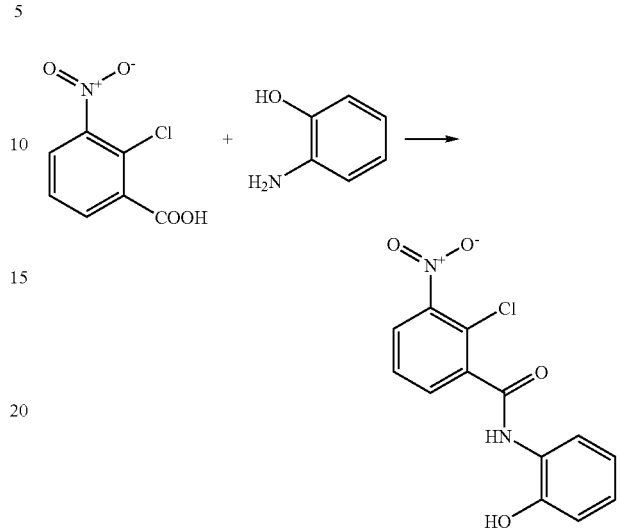

To a suspension of 7.8 g (38.7 mmole) of 2-chloro-3-nitrobenzoic acid in 100 mL of methylene chloride was added 5 drops of DMF and 4.35 mL (50 mmole) of oxalyl chloride. The reaction mixture was stirred at 22° C. for 2 hours. The solution was then concentrated under reduced pressure. The residue was dissolved in 75 mL of toluene, and this solution was added dropwise to a stirred mixture of 4.4 g (40 mmole) of 2-aminophenol and 11 g (.1 mole) of sodium carbonate in 50 mL of water and 50 mL of toluene. The reaction mixture was stirred at 22° C. for 16 hours. The reaction mixture was diluted with 50 mL of water and the precipitated solid was collected, washed with water and dried in vacuo to provide 9.75 g (86% yield) of the title compound. M.p. 158–159° C.

Example 2

This example illustrates a process for producing 4-nitro-10H-dibenzo[b,f][1,4]oxazepin-11-one.

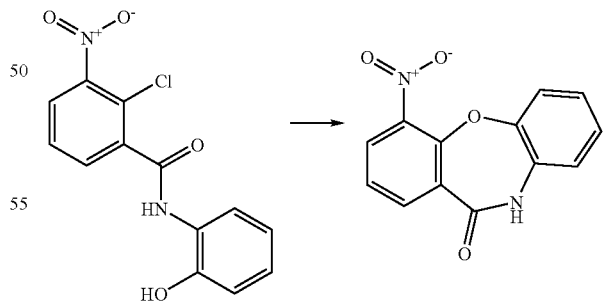

A mixture of 5 g (17.1 mmole) of 2-chloro-N-(2-hydroxyphenyl)-3-nitro-benzamide and 0.8 g (20 mmole) of sodium hydroxide in 100 mL of water was heated under reflux for 2.5 hours. The mixture was chilled in an ice bath for 0.5 hour and the precipitated solid was collected, washed with water and dried in vacuo to give 4.03 g (91% yield) of the title compound. M.p. 298–301° C.

Example 3

This example illustrates a process for producing 4-amino-10H-dibenzo[b,f][1,4]oxazepin-11-one hydrochloride.

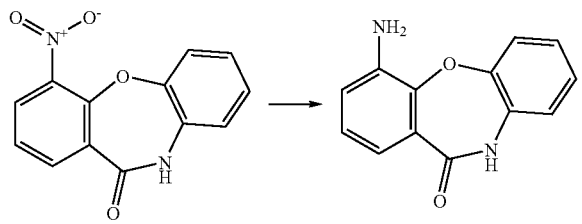

A mixture of 5 g of 4-nitro-10H-dibenzo[b,f][1,4]oxazepin-11-one, 1 g of 10% palladium on carbon, and 3.25 mL (19.5 mmole) of 6 N hydrochloric acid in 400 mL of methanol was shaken under 45 psi hydrogen pressure at 22° C. for 3 hours. The catalyst was removed by filtration and washed with 1 L of methanol. The filtrate and washings were combined and concentrated under reduced pressure. The residue was triturated with 50 mL of ethanol. To this solution was slowly added 50 mL of ethyl ether and the crystalline product was collected and dried in vacuo to give the title compound (5.1 g, 99% yield). M.p. 266–268° C.

Example 4

This example illustrates a process for producing 10-benzyl-4-nitro-10H-dibenzo[b,f][1,4]oxazepin-11-one.

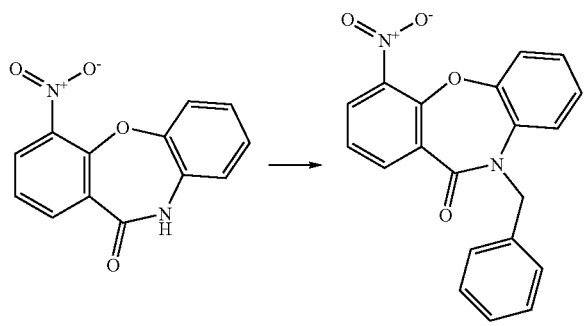

To a mixture of 0.64 g (2.5 mmole) of 4-nitro-10H-dibenzo[b,f][1,4]oxazepin-11-one and 1 g of powdered potassium carbonate in 7 mL of DMF was added 0.3 mL (2.5 mmole) of benzyl bromide. The reaction mixture was stirred at 22° C. for 16 hours. The solvent was removed under reduced pressure and the residue was partitioned between 10 mL of water and 50 mL of ethyl acetate. The organic phase was dried (magnesium sulfate) and concentrated under reduced pressure. The residue was subjected to low-pressure column chromatography over 100 g silica gel (230–400 mesh) eluting with 15% ethyl acetate in hexane. Product fractions were combined and concentrated under reduced pressure to provide the title compound as a heavy syrup (0.88 g, 88% yield). M+H=347.

Example 5

This example illustrates a process for producing 4-amino-10-benzyl-10H-dibenzo[b,f][1,4]oxazepin-11-one hydrochloride.

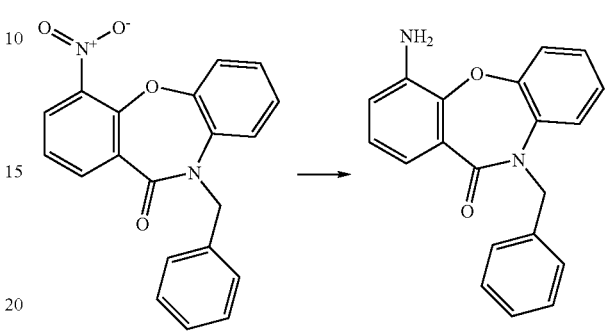

A mixture of 0.8 g (2.31 mmole) of 10-benzyl-4-nitro-10H-dibenzo[b,f][1,4]oxazepin-11-one and 0.3 g of 10% palladium on carbon in 35 mL of methanol was hydrogenated at 50 psi at 22° C. for 3 hours. The catalyst was removed by filtration and the filtrate was reduced to about 5 mL under reduced pressure. The pH of the solution was adjusted to about pH 2 by addition of 1.0 M hydrogen chloride in ethyl ether. The mixture was concentrated under reduced pressure and the residue was recrystallized from methanol/ethyl acetate/ethyl ether to provide the title compound (0.407 g, 50% yield). M.p. 221–222° C.

Example 6

This example illustrates a process for producing 4-piperazin-1-yl-10H-dibenzo[b,f][1,4]oxazepin-11-one, hydrochloride.

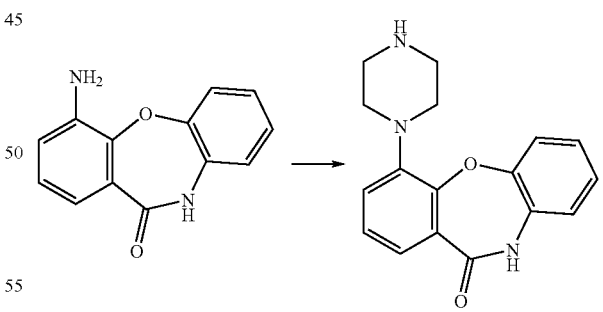

A mixture of 3.6 g (20 mmole) of bis-(2-chloroethyl)amine hydrochloride and 5 g of 4-amino-10H-dibenzo[b,f][1,4]oxazepin-11-one hydrochloride was immersed in a preheated 260° C. oil bath. The reaction mixture was heated at 260–270° C. for 13 minutes. The dark residue was dissolved in 200 mL of hot methanol and the volume was reduced to about 50 mL by distillation. The light brown crystalline solid was collected and dried in vacuo to give 5.5 g (87% yield) of the title compound. M.p. 326–327° C., M+H=296.

Example 7

This example illustrates a process for producing 10-benzyl-4-piperazin-1-yl-10H-dibenzo[b,f][1,4]oxazepin-11-one.

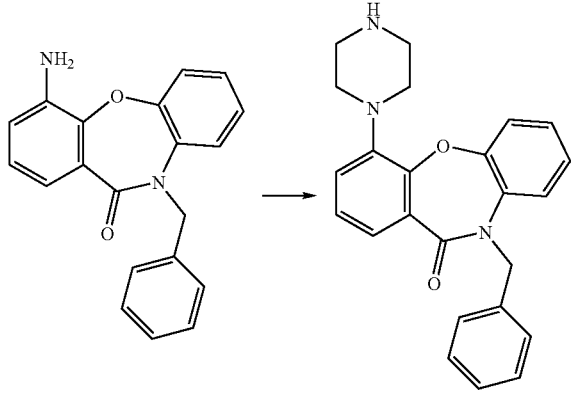

A solution of 0.3 g (0.95 mmole) of 4-amino-10-benzyl-10H-dibenzo[b,f][1,4]oxazepin-11-one, hydrochloride and 0.17 g (0.95 mmole) of bis-(2-chloroethyl)amine, hydrochloride in 2 mL of methanol was prepared. The solvent was removed under reduced pressure. The residue was heated at 250° C. for 1 minute. The glassy residue was subjected to low-pressure column chromatography over silica gel (230–400 mesh) eluting with 3% methanol in chloroform containing 0.25% of conc. ammonium hydroxide. Product fractions were combined and concentrated under reduced pressure and the residue was recrystallized from ethyl ether/hexane to provide the title compound (0.14 g, 38% yield). M.p. 198–199° C. M+H=386.

Example 8

This example illustrates a process for producing 4-(4-benzylpiperazin-1-yl)-10H-dibenzo[b,f][1,4]oxazepin-11-one.

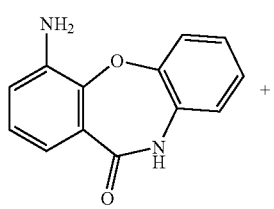

+

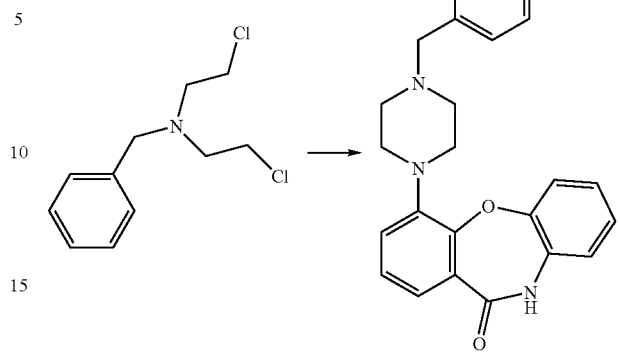

A mixture of 0.062 g (0.24 mmole) of 4-amino-10H-dibenzo[b,f][1,4]oxazepin-11-one, hydrochloride and 0.062 g (0.23 mmole) of benzyl-bis-(2-chloroethyl)-amine hydrochloride was heated at 240° C. for 1 minute. The dark, glassy residue was subjected to low-pressure column chromatography over silica gel (230–400 mesh) eluting with 1% methanol in chloroform. Product fractions were combined and concentrated under reduced pressure to give the title compound as a crystalline solid (0.030 g, 32% yield). M.p. 201–202° C.

Example 9

This example illustrates a process for producing tert-butyl-[4-(11-oxo-10,11-dihydro-dibenzo[b,f][1,4]oxazepin-4-yl)-piperazine-1-]-carboxylate.

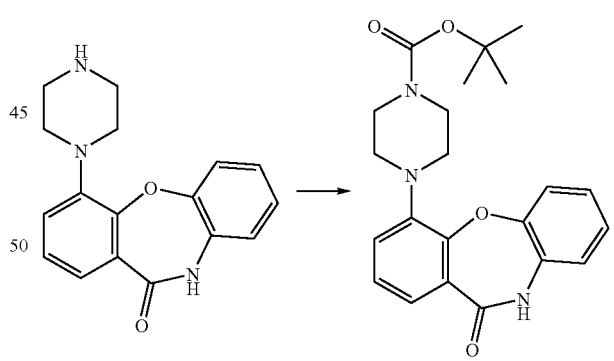

To a stirred mixture of 0.87 g (2.62 mmole) of 4-piperazin-1-yl-10H-dibenzo[b,f][1,4]oxazepin-11-one, hydrochloride and 0.59 g (2.7 mmole) of di-tert-butyl dicarbonate in 50 mL of THF was added 2 mL of pyridine, 5 mg of 4-dimethylaminopyridine and 0.5 mL of triethylamine (i.e., TEA). The reaction mixture was stirred at 22° C. for 1 hour. The mixture was concentrated under reduced pressure and the residue was partitioned between 50 mL of ethyl acetate and 20 mL of water. The organic phase was washed with 10 mL of saturated sodium chloride, dried (magnesium sulfate)

and concentrated under reduced pressure. The residue was recrystallized from ethyl ether to provide the title compound (0.902 g, 87% yield). M.p. 231–232° C. M+H=396.

Example 10

This example illustrates a process for producing 4-[10-(4-fluoro-benzyl)-11-oxo-10,11-dihydro-dibenzo[b,f][1,4]oxazepin-4-yl]-piperazine-1-carboxylic acid, tert-butyl ester.

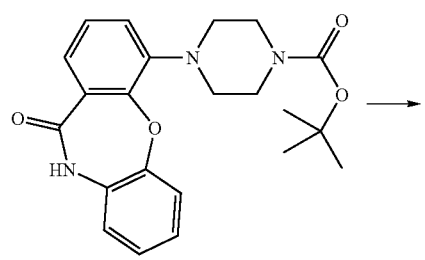

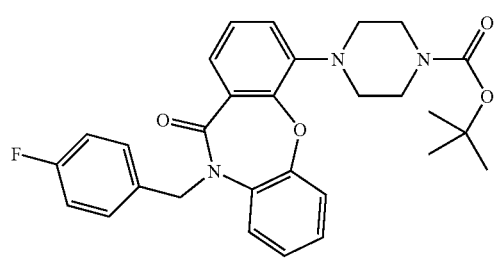

A mixture of 0.05 g (0.126 mmole) of tert-butyl-[4-(11-oxo-10,11-dihydro-dibenzo[b,f][1,4]oxazepin-4-yl)-piperazine-1-]-carboxylate, 0.050 g (0.4 mmole) of powdered potassium carbonate and 0.1 mL (0.8 mmole) of 4-fluorobenzyl bromide in 1.5 mL of DMF was stirred under a nitrogen atmosphere at 22° C. for 16 hours. The mixture was diluted with 10 mL of water and extracted with 30 mL of ethyl ether. The organic phase was washed with 2×10 mL water, dried (magnesium sulfate) and concentrated under reduced pressure. A homogenous syrup remained (0.06 g, 94% yield). M+H=504.

Example 11

This example illustrates a process for producing 4-[10-(3-fluoro-benzyl)-11-oxo-10,11-dihydro-dibenzo[b,f][1,4]oxazepin-4-yl]-piperazine-1-carboxylic acid, tert-butyl ester.

Using the procedure of Example 10, 4-[10-(3-fluoro-benzyl)-11-oxo-10,11-dihydro-dibenzo[b,f][1,4]oxazepin-4-yl]-piperazine-1-carboxylic acid, tert-butyl ester was prepared from the appropriate starting materials.

Example 12

This example illustrate a process for producing 10-(4-fluoro-benzyl)-4-piperazin-1-yl-10H-dibenzo[b,f][1,4]oxazepin-11-one, dihydrochloride.

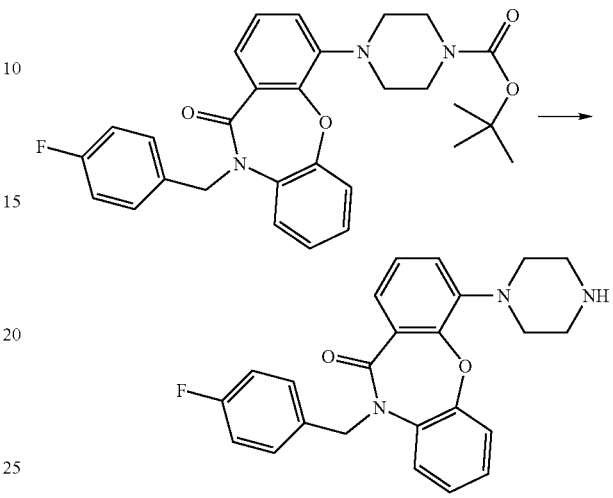

A solution of 0.06 g (0.12 mmole) of 4-[10-(4-fluoro-benzyl)-11-oxo-10,11-dihydro-dibenzo[b,f][1,4]oxazepin-4-yl]-piperazine-1-carboxylic acid, tert-butyl ester in 2 mL of ethanol containing 2 mL of 6 N hydrochloric acid was heated under reflux for 0.25 hour. The solution was concentrated under reduced pressure and the residue was recrystallized from ethanol/ethyl acetate/ether to provide the title compound (0.0465 g, 81% yield). M.p. 214–216° C.

Examples 13–15

Using the procedure of Example 12, the following compounds were also prepared from the appropriate starting materials.

10-(3-fluoro-benzyl)-4-piperazin-1-yl-10H-dibenzo[b,f][1,4]oxazepin-11-one, dihydrochloride. M.p. 191–192° C., M+H=404;

10-(2-fluoro-benzyl)-4-piperazin-1-yl-10H-dibenzo[b,f][1,4]oxazepin-11-one, dihydrochloride; and 4-piperazin-1-yl-10-(3-trifluoromethyl-benzyl)-10H-dibenzo[b,f][1,4]oxazepin-11-one, dihydrochloride.

Example 16

This example illustrates a process for producing 4-amino-5,10-dihydro-dibenzo[b,e][1,4]diazepin-11-one, hydrochloride.

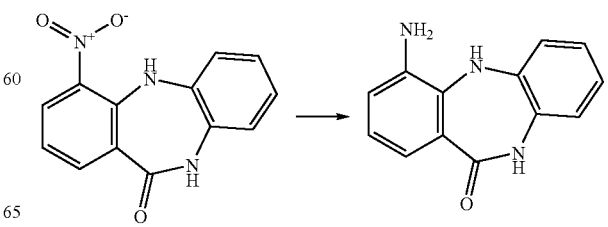

A mixture of 0.227 g (0.9 mmole) of 4-nitro-5,10-dihydro-dibenzo[b,e][1,4]diazepin-11-one[prepared according to Breslin, et al, *J. Med. Chem.*, 1995, 38,771] and 0.5 mL of 6 N hydrochloric acid in 30 mL of ethanol was hydrogenated over 0.05 g of 10% palladium on carbon at 22° C. and 50 psi for 3 hours. The catalyst was removed by filtration and the filtrate was concentrated under reduced pressure. The residue was triturated with 1 mL of ethanol and 3 mL of ethyl acetate. The light green crystalline solid was collected and dried in vacuo to provide the title compound (0.229 g, 97% yield). M.p. 270–272° C. (dec.). M+H=226.

Example 17

This example illustrates a process for producing 4-piperazin-1-yl-5,10-dihydro-dibenzo[b,e][1,4]diazepin-11-one, dihydrochloride.

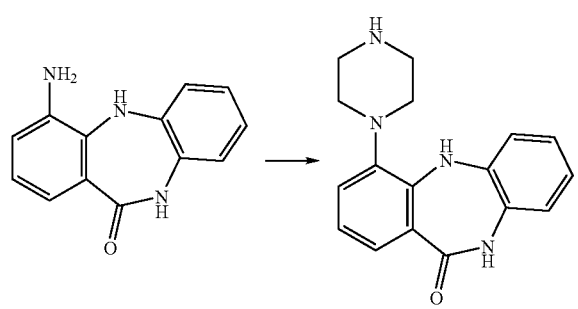

A mixture of 0.05 g (0.9 mmole) of 4-amino-5,10-dihydro-dibenzo[b,e][1,4]diazepin-11-one, hydrochloride and 0.036 g (0.2 mmole) of bis-(2-chloroethyl)amine, hydrochloride was heated at 260° C. in a sealed tube for 4 minutes. The residue was recrystallized from methanol to provide the title compound as a light tan solid (0.029 g, 46% yield). M.p. 360° C. (dec.). M+H=295.

Example 18

This example illustrates a process for producing 4-(11-Oxo-10,11-dihydro-5H-dibenzo[b,f][1,4]diazepin-4-yl)-piperazine-1-carboxylic acid tert-butyl ester.

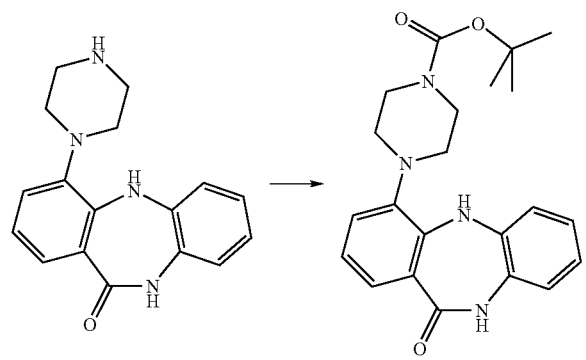

To a suspension of 0.25 grams (0.76 mmole) 4-piperazin-1-yl-5,10-dihydro-dibenzo[b,f][1,4]diazepin-11-one dihydrochloride in 10 mL tetrahydrofuran was added 0.175 gram (0.8 mmole) di-tert-butyl dicarbonate and 0.3 mL (2.0 mmole) triethylamine. The reaction mixture was stirred at 230 for 5 hours. The solvent was removed under reduced pressure and the residue was partitioned between 50 mL chloroform and 15 mL 10% sodium bicarbonate. The organic phase was dried (magnesium sulfate) and concentrated under reduced pressure. The residue was recrystallized from ether/hexane to provide the title compound, 0.23 gram (77%), m.p. 264–265°, M$^+$H=395.

Example 19

This example illustrates a process for producing 4-(10-Benzyl-11-oxo-10,11-dihydro-5H-dibenzo[b,f][1,4]diazepin-4-yl)piperazine-1-carboxylic acid tert-butyl ester.

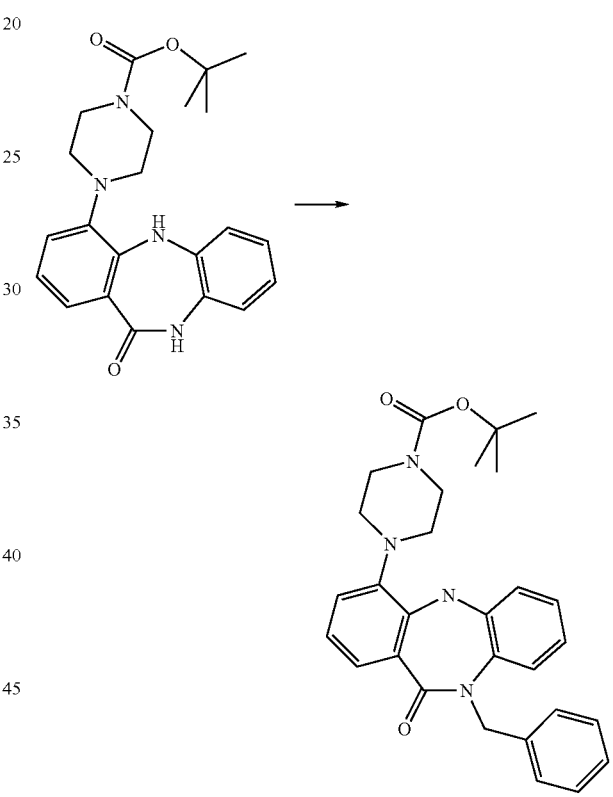

A mixture of 0.211 grams (0.535 mmole) 4-(11-oxo-10,11-dihydro-5H-dibenzo[b,f][1,4]diazepin-4-yl)-piperazine-1-carboxylic acid tert-butyl ester, 0.6 mL 1.0M potassium tert-butoxide in THF, and 0.064 mL (0.54 mmole) benzyl bromide in 3.0 mL DMF was stirred at 23° for 2 hours. The reaction mixture was diluted with 10 mL water and extracted with 35 mL ethyl acetate. The organic phase was dried (magnesium sulfate) and concentrated under reduced pressure. The residue was subjected to low pressure column chromatography over silica gel 230–400 mesh eluting with 15% ethyl acetate in hexane. Product fractions were combined and concentrated under reduced pressure to leave the title compound as a white solid, 0.08 grams, m.p. 109–110°, M$^+$H=485.

Example 20

This example illustrates a process for producing 10-Benzyl-4-piperazin-1-yl-5,10-dihydro-dibenzo[b,f][1,4]diazepin-11-one dihydrochloride.

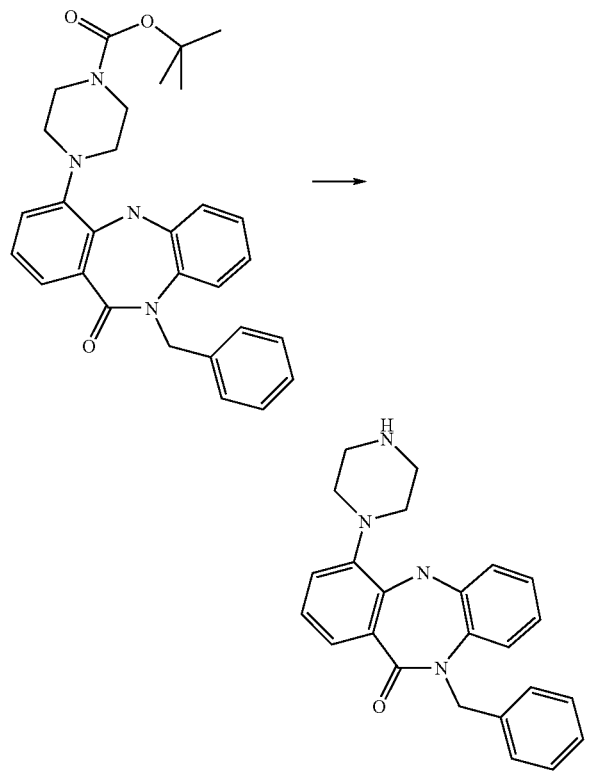

To a solution of 0.06 gram (0.123 mmole) 4-(10-benzyl-11-oxo-10,11-dihydro-5H-dibenzo[b,f][1,4]diazepin-4-yl) piperazine-1-carboxylic acid tert-butyl ester in 5.0 mL ethanol was added 1.0 mL 6N hydrochloric acid. The reaction mixture was heated under reflux for 3 minutes, then the solution was concentrated under reduced pressure and the residue was recrystallized from ethanol/ether to provide the title compound, 0.061 gram, m.p. 322–323° (dec), M+H=385.

Example 21

This example illustrates a process for producing 2-Bromo-N-(2-mercapto-phenyl)-3-nitro-benzamide.

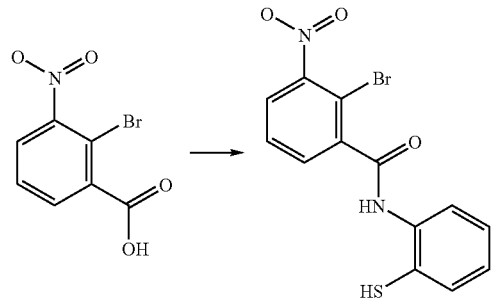

To a solution of 3.0 grams (12.2 mmole) 2-bromo-3-nitrobenzoic acid in 50 mL dichloromethane was added 1.6 mL (18 mmole) oxalyl chloride and 4 drops DMF. The reaction mixture was stirred at 23° for 2 hours. The solution was concentrated under reduced pressure and the residue was dissolved in 40 mL toluene. This solution was added dropwise to a stirred mixture of 1.4 mL (13 mmole) 2-aminobenzenethiol and 1.7 grams sodium bicarbonate (20 mmole) in 35 mL toluene and 35 mL water at 0°. The reaction mixture was stirred at 0° for 3 hours. The solid that precipitated at the interface was collected, washed with water, then hexane and dried to provide the title compound, 3.52 grams, (82%) m.p. 152–153°.

Example 22

This example illustrates a process for producing 4-nitro-10H-dibenzo[b,f][1,4]thiazepin-11-one.

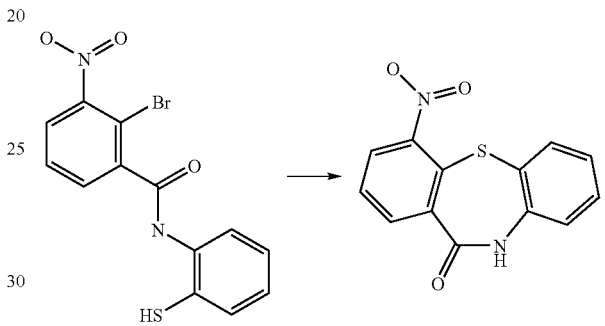

To a solution of 3.52 grams (10 mmole) 2-bromo-N-(2-mercapto-phenyl)-3-nitro-benzamide in 100 mL acetonitrile was added 2.0 Ml (11 mmole) diisopropylethyl amine. The reaction mixture was heated under reflux for 16 hours. The solution was concentrated under reduced pressure. To the residue was added 10 mL ethyl acetate and 10 mL water. The mixture was stirred at 23° for 0.5 hour. The resulting light yellow solid was collected, washed with water, ethyl acetate and hexane and dried to provide the title compound, 2.12 grams, (78%), m.p. 259–261°.

Example 23

This example illustrates a process for producing 10-Benzyl-4-nitro-10H-dibenzo[b,f][1,4]thiazepin-11-one.

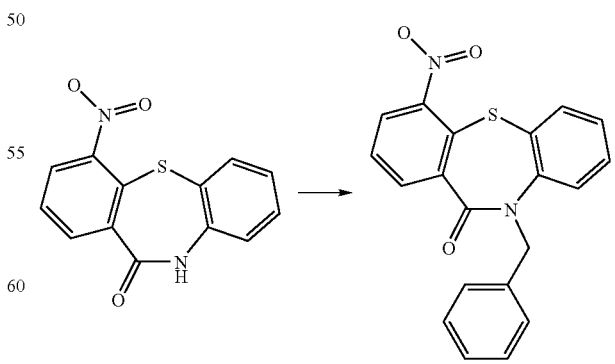

A mixture of 1.0 gram (3.7 mmole) 4-nitro-10H-dibenzo[b,f][1,4]thiazepin-11-one, 0.828 gram (6 mmole) potassium carbonate and 0.45 mL (3.75 mmole) benzyl bromide in 10 mL DMF was stirred at 23° for 4 hours. The solution was concentrated under reduced pressure and the residue was partitioned between 200 mL ethyl acetate and 50 mL water. The organic phase was dried (magnesium sulfate) and concentrated under reduced pressure. The residue was recrystallized from ethyl ether to provide the title compound, 0.796 gram, (58%) m.p. 223–224°.

Example 24

This example illustrate a process for producing 4-Amino-10-benzyl-10H-dibenzo[b,f][1,4]thiazepin-11-one hydrochloride.

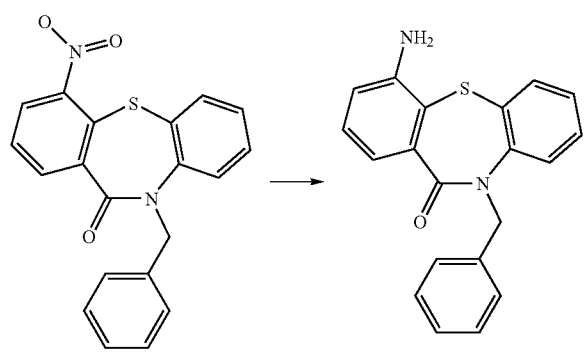

A mixture of 0.225 gram (0.62 mmole) 10-benzyl-4-nitro-10H-dibenzo[b,f][1,4]thiazepin-11-one, 0.06 gram 10% palladium on carbon and 0.5 mL 6N hydrochloric acid in 10 mL ethanol was hydrogenated under 50 psi hydrogen gas at 23° for 2 hours. The mixture was filtered and concentrated under reduced pressure. The residue was recrystallized from methanol/ether to provide the title compound, 0.129 gram, m.p. 219–220°, M$^+$H=333.

Example 25

This example illustrates a process for producing 10-Benzyl-4-piperazin-1-yl-10H-dibenzo[b,f][1,4]thiazepin-11-one dihydrochloride monohydrate.

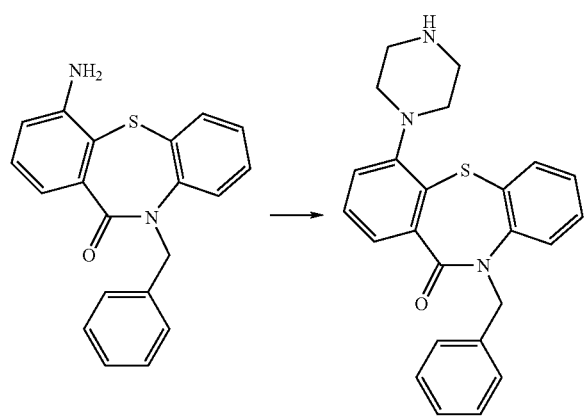

An intimate mixture of 0.1 gram (0.27 mmole) 4-amino-10-benzyl-10H-dibenzo[b,f][1,4]thiazepin-11-one hydrochloride and 0.073 gram (0.41 mmole) bis-2-(chloroethyl) amine hydrochloride was immersed in a preheated 260° oil bath. The reaction mixture was heated at 260° for 3 minutes. The dark glassy residue was subjected to low pressure column chromatography over silica gel 230–400 mesh eluting with 5% methanol in chloroform containing 0.25% concentrated ammonium hydroxide. Product fractions were combined and concentrated under reduced pressure. The residue was converted to the hydrochloride salt and recrystallized from methanol/ethyl acetate/ether to provide the title compound, 0.074 grams, (65%), m.p. 301–302° M$^+$H=402.

Example 26

This example illustrates a process for producing 3-Bromo-2-iodo-5-methyl benzoic acid.

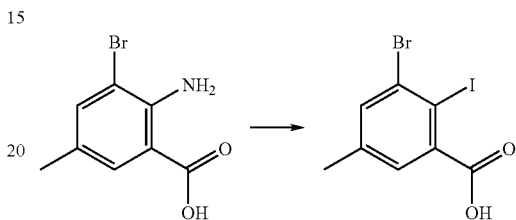

Twenty grams (0.87 mole) 2-amino-3-bromo-5-methyl benzoic acid was suspended in 120 mL water with mechanical stirring. The mixture was cooled in an ice bath and 100 mL concentrated sulfuric acid was added slowly. A solution of 12 grams (0.141 mole) sodium nitrite in 100 mL water was added dropwise over 0.5 hour. The reaction mixture was stirred for an additional 0.25 hour at 0–5°. The mixture was poured into a well-stirred solution of 24 grams (0.145 mole) potassium iodide in 100 mL water. The resulting solid was collected by filtration and stirred in 200 mL ethyl acetate. A solution of 200 mL 20% sodium hydrogen sulfite was added slowly. The organic layer was separated, washed with 100 mL 20% sodium hydrogen sulfite, 50 mL saturated sodium chloride, dried (magnesium sulfate) and concentrated under reduced pressure. The residue was recrystallized from ether/hexane to provide the title compound, 15 grams, m.p. 152–153°.

Example 27

This example illustrates a process for producing 3-Bromo-N-(2-hydroxy-phenyl)-2-iodo-5-methyl-benzamide.

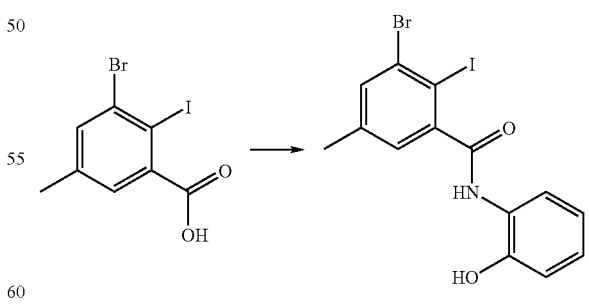

To a solution of 5.0 grams (14.7 mmole) 3-bromo-2-iodo-5-methyl benzoic acid in 150 mL dichloromethane was added 5 drops DMF and 3.0 mL (34.5 mmole) oxalyl chloride. The reaction mixture was stirred at 23° for 2 hours. The solution was concentrated under reduced pressure. The residue was dissolved in 100 mL toluene and 50 mL 10% sodium bicarbonate and 1.6 grams (14.7 mmole) 2-aminophenol were added. The mixture was stirred at 23° for 16 hours. The precipitate was collected, washed with water, toluene, hexane, and dried to provide the title compound, 6 grams (95%), m.p. 225–226°.

Example 28

This example illustrates a process for producing 4-Bromo-2-methyl-10H-dibenzo[b,f][1,4]oxazepin-11-one.

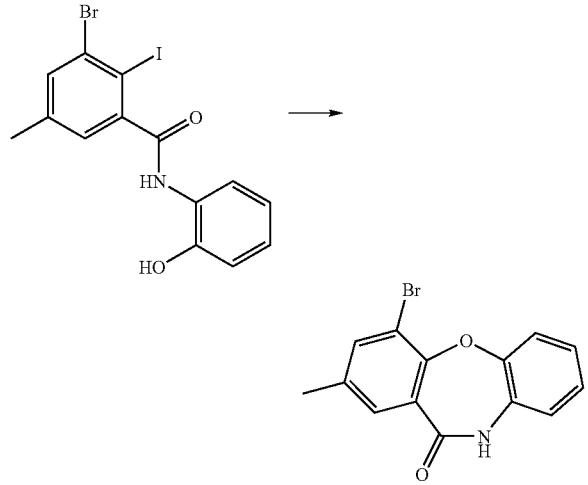

To a solution of 6.45 grams (14.9 mmole) 3-bromo-N-(2-hydroxy-phenyl)-2-iodo-5-methyl-benzamide in 25 mL THF was added 15 mL 1.0 M potassium tert-butoxide in THF. The solution was concentrated under reduced pressure and the residue was dissolved in 15 mL DMF. The reaction mixture was heated under reflux for 20 hours. The mixture was diluted with 100 mL water. Ethyl acetate was added (200 mL) and the mixture was filtered. The organic phase was extracted with 50 mL 5% sodium hydroxide, then it was washed with 25 mL saturated sodium chloride, dried (magnesium sulfate) and concentrated under reduced pressure. The residue was subjected to low pressure column chromatography over silica gel 230–400 mesh eluting with 15% ethyl acetate in hexane. Product fractions were combined and concentrated under reduced pressure. The residue was recrystallized from ether/hexane to provide the title compound, 1.36 grams (30%), m.p. 223–224°.

Example 29

This example illustrates a process for producing 10-Benzyl-4-bromo-2-methyl-10H-dibenzo[b,f][1,4] oxazepin-11-one.

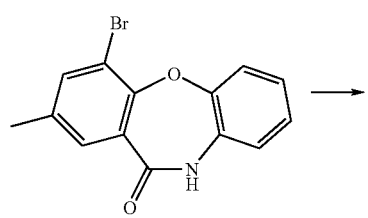

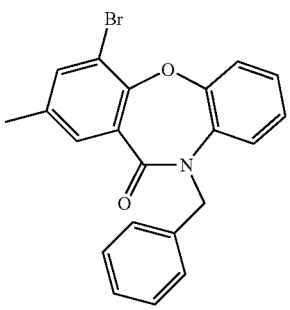

To a solution of 0.5 gram (1.64 mmole) 4-bromo-2-methyl-10H-dibenzo[b,f][1,4]oxazepin-11-one in 5 mL DMF was added 0.1 gram (2.5 mmole) 100% sodium hydride. After 5 minutes, 0.2 mL (1.7 mmole) benzyl bromide was added. The reaction mixture was stirred at 23° for 2 hours. The solution was concentrated under reduced pressure and the residue was partitioned between 20 mL water and 50 mL ethyl acetate. The organic phase was dried (magnesium sulfate) and concentrated under reduced pressure. The residue was subjected to low pressure column chromatography over silica gel 230–400 mesh eluting with 5% ethyl acetate/hexane. Product fractions were combined and concentrated under reduced pressure to provide the title compound as a heavy oil, 0.46 gram (71%), $M^+H=394$.

Example 30

This example illustrates a process for producing 4-(10-Benzyl-2-methyl-11-oxo-10,11-dihydro-dibenzo[b,f][1,4] oxazepin-4-yl)-3,6-dihydro-2H-pyridine-1-carboxylic benzyl ester.

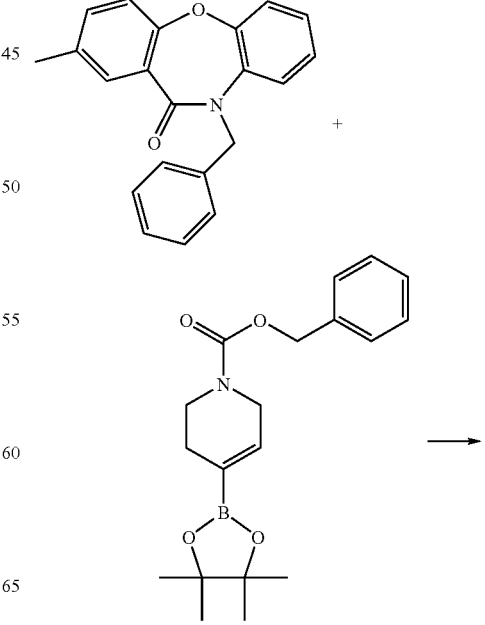

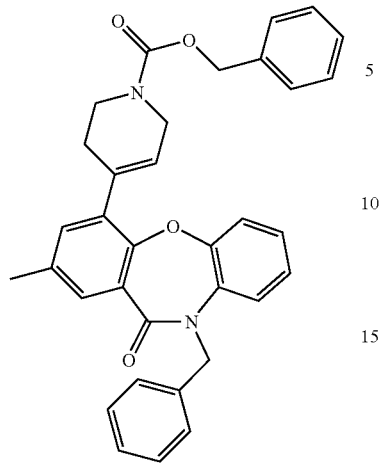

A mixture of 0.43 gram (1.09 mmole) 10-benzyl-4-bromo-2-methyl-10H-dibenzo[b,f][1,4]oxazepin-11-one, 0.374 gram (1.09 mmole) 4-(4,4,5,5-tetramethyl-[1,3,2]dioxaborolan-2-yl)-3,6-dihydro-2H-pyridine-1-carboxylic acid benzyl ester (P. R. Eastwood, Tetrahedron Letters 41: 3705–3708 (2000)), 0.451 gram (3.27 mmole) potassium carbonate, and 0.054 gram (0.065 mmole) [1,1'-bis(diphenylphosphino)-ferrocene]dichloropalladium(II) complex with dichloromethane (1:1) in 5 mL DMF was heated at 80° for 3 hours. The mixture was concentrated under reduced pressure. To the residue was added 50 mL ethyl acetate and 10 mL chloroform. The mixture was filtered and concentrated under reduced pressure. The residue was partitioned between 100 mL ethyl acetate and 20 mL saturated sodium chloride. The organic phase was dried and concentrated under reduced pressure. The residue was subjected to low pressure column chromatography over silica gel 230–400 mesh eluting with 20% ethyl acetate in hexane. The title compound was obtained as a foam, 0.366 gram (63%), M$^+$H=531.

Example 31

This example illustrates a process for producing 10-Benzyl-2-methyl-4-piperidin-4-yl-10H-dibenzo[b,f][1,4]oxazepin-11-one hydrochloride.

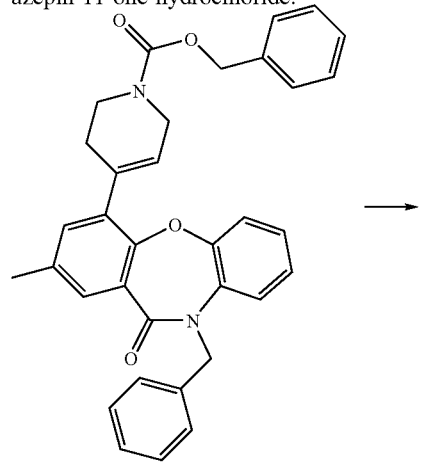

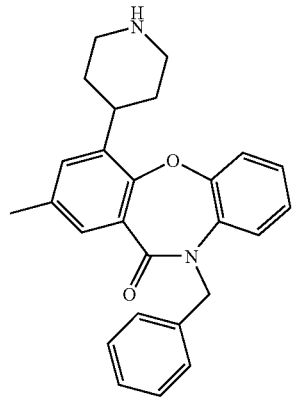

A mixture of 0.235 gram (0.44 mmole) 4-(10-benzyl-2-methyl-11-oxo-10,11-dihydro-dibenzo[b,f][1,4]oxazepin-4-yl)-3,6-dihydro-2H-pyridine-1-carboxylic benzyl ester and 75 mg 10% palladium on carbon in 8 mL methanol was hydrogenated at 50 psi hydrogen at 23° for 72 hours. The mixture was filtered and concentrated under reduced pressure. The residue was subjected to low pressure column chromatography over silica gel 230–400 mesh eluting with 5% methanol in chloroform containing 0.25% concentrated ammonium hydroxide. The title compound was obtained and converted to the hydrochloride salt, as a white foam, 0.101 gram (53%), M$^+$H=399.

Example 32

This example illustrates a process for producing 4-(11-Oxo-10,11-dihydro-dibenzo[b,f][1,4]oxazepin-4-yl)-piperazine-1-carboxylic acid benzyl ester.

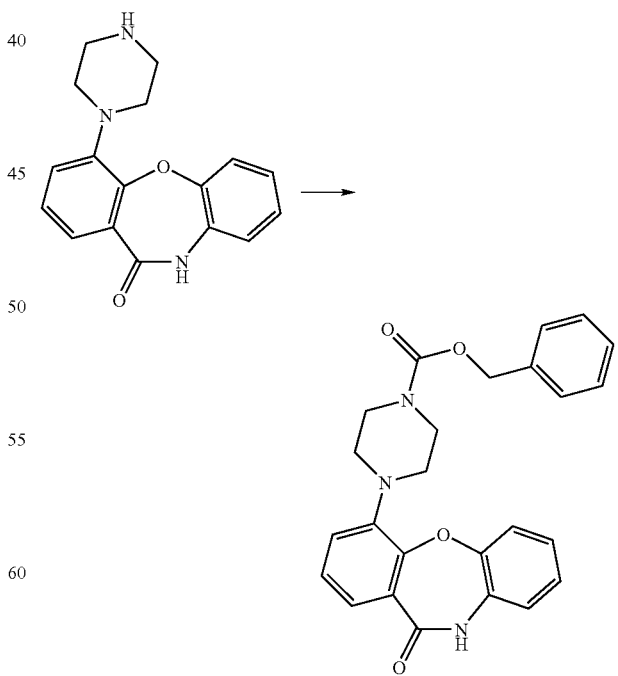

To 0.67 gram 4-piperazin-1-yl-10H-dibenzo[b,f][1,4]oxazepin-11-one hydrochloride and 2.0 grams (14.5 mmole)

potassium carbonate in 20 mL toluene and 10 mL water was added 0.3 mL benzyl chloroformate. To this mixture was added 3.0 mL 4M sodium hydroxide and 5 mL THF. The reaction mixture was stirred at 23° for 2 hours. The reaction mixture was extracted with 30 mL ethyl acetate. The organic phase was washed with 10 mL saturated sodium chloride, dried (magnesium sulfate) and concentrated under reduced pressure. The title compound was obtained as a crystalline solid from ether/hexane, 0.597 gram (70%), m.p. 212–213°, M+H=430.

Example 33

This example illustrates a process for producing 3-[4-(4-Benzyloxycarbonyl-piperazin-1-yl)-11-oxo-11H-dibenzo[b,f][1,4]oxazepin-10-ylmethyl]-indole-1-carboxylic acid tert-butyl ester.

A mixture of 0.4 gram (0.93 mmole) 4-(11-oxo-10,11-dihydro-dibenzo[b,f][1,4]oxazepin-4-yl)-piperazine-1-carboxylic acid benzyl ester and 0.414 gram (3.0 mmole) powdered potassium carbonate in 3.0 mL DMF was stirred at 23° for 5 minutes. To this was added 0.29 g (0.93 mmole) 3-bromomethyl-indole-1-carboxylic acid tert-butyl ester (prepared following T. K. Venkatachalam, et al, OPPI Briefs Vol. 25, No. 2, pp. 249–251 (1993)). The reaction mixture was stirred at 23° for 16 hours. Another 0.15 g (0.48 mmole) 3-bromomethyl-indole-1-carboxylic acid tert-butyl ester was added and the mixture was stirred for an additional 4 hours. To the mixture was added 25 mL water. The precipitate was collected and dissolved in 30 mL chloroform. The solution was washed with 20 mL water, dried (magnesium sulfate) and concentrated under reduced pressure. The residue was recrystallized from ethyl acetate/ether to afford the title compound, 0.365 gram (60%), m.p. 205–206°, M+H=659.

Example 34

This example illustrates a process for producing 10-(1H-Indol-3-ylmethyl)-4-piperazin-1-yl-10H-dibenzo[b,f][1,4]oxazepin-11-one.

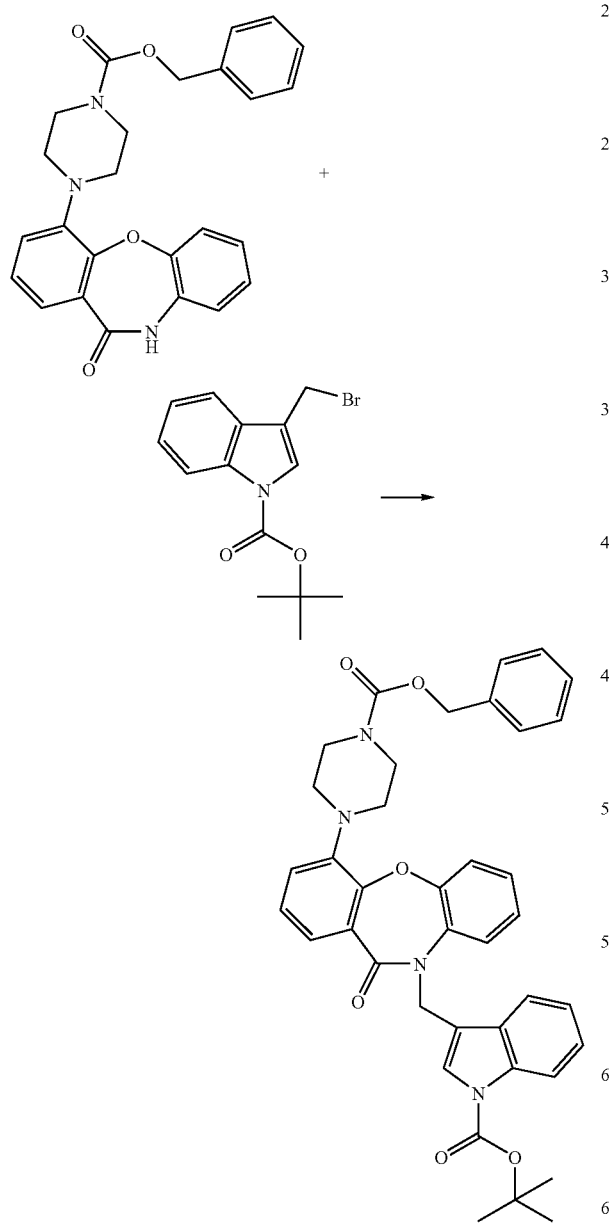

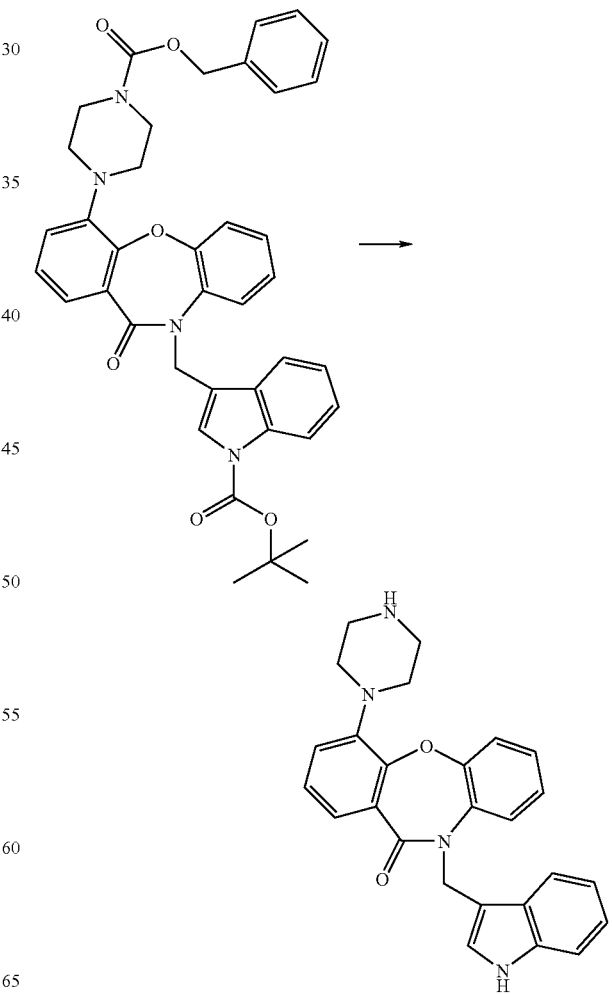

Neat 3-[4-(4-benzyloxycarbonyl-piperazin-1-yl)-11-oxo-11H-dibenzo[b,f][1,4]oxazepin-10-ylmethyl]-indole-1-carboxylic acid tert-butyl ester (0.178 gram, 0.27 mmole) was immersed in a preheated 220° oil bath. The reaction mixture was heated at 220° under a nitrogen atmosphere for 10 minutes. The glassy residue was dissolved in a mixture of 1.0 mL ethyl acetate and 3 mL methanol. To the solution was added a suspension of 0.1 gram 10% palladium on carbon in 3.0 mL ethanol. To this was added 5 mL THF and the mixture was hydrogenated under 45 psi hydrogen gas at 23° for 16 hours. The mixture was filtered and concentrated under reduced pressure. The residue was subjected to low pressure column chromatography over silica gel 230–400 mesh eluting with 3% methanol in chloroform saturated with concentrated ammonium hydroxide. The title compound was isolated as the free base, 0.050 gram (44%), m.p. 98–99° M+H=425.

Example 35

This example illustrates a process for producing 4-(4-Methyl-piperazin-1-yl)-10,11-dihydro-dibenzo[b,f][1,4]oxazepine.

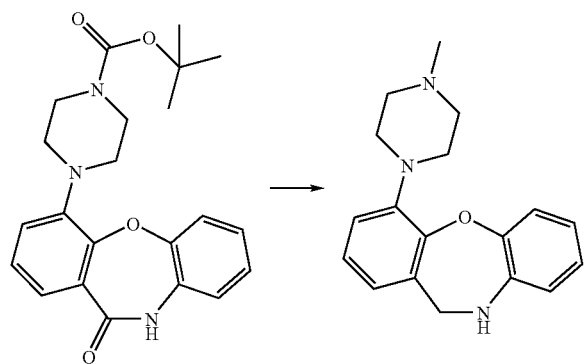

To a solution of 0.442 gram (1.12 mmole) tert-butyl-[4-(11-oxo-10,11-dihydro-dibenzo[b,f][1,4]oxazepin-4-yl)-piperazine-1-]-carboxylate in 10 mL THF was added 3.0 mL 1.0 M lithium aluminum hydride in THF. The reaction mixture was heated under reflux for 2 hours. Excess water was added dropwise to the mixture. The mixture was filtered and concentrated under reduced pressure. The residue was taken up in 5 mL 6N hydrochloric acid and washed with two 20 mL portions of ether. The aqueous phase was cooled in an ice bath and the pH was adjusted to 12 with 50% w/w sodium hydroxide. The mixture was extracted with 50 mL 50% ethyl acetate/ether. The organic phase was dried (magnesium sulfate) and concentrated under reduced pressure. The title compound was obtained as the solid free base, m.p. 119–120°, M+H=296.

Example 36

This example illustrates a process for producing 10-Benzenesulfonyl-4-(4-methyl-piperazin-1-yl)-10,11-dihydro-dibenzo[b,f][1,4]oxazepine hydrochloride.

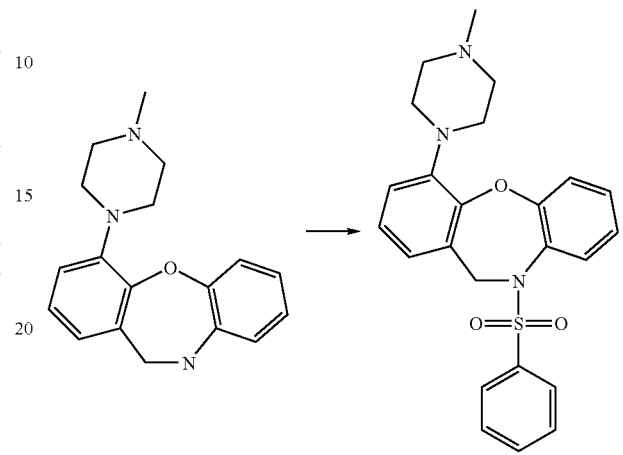

To a solution of 0.3 gram (1.0 mmole) 4-(4-methyl-piperazin-1-yl)-10,11-dihydro-dibenzo[b,f][1,4]oxazepine in 2 mL THF and 4 mL chloroform was added ) 0.03 gram dimethylpyridine-4-yl-amine, 0.15 mL triethylamine and 0.14 mL benzenesulfonyl chloride. The reaction mixture was stirred at 23° for 72 hours. Each day, another 0.1 mL benzenesulfonyl chloride and 0.03 gram DMAP was added. The solution was concentrated under reduced pressure. The residue was partitioned between 30 mL ethyl acetate and 10 mL 10% sodium carbonate. The organic phase was dried (magnesium sulfate) and concentrated under reduced pressure. The residue was subjected to low pressure column chromatography over silica gel 230–400 mesh eluting with 5 ethyl acetate:4.5 hexane:0.5 methanol containing 0.25% concentrated ammonium hydroxide. The title compound was recrystallized from methanol/ethyl acetate/ether, 0.139 gram (30%), m.p. 242–243°, M+H=436.

Example 37

Formulations

This example illustrates a variety of formulation compositions.

Pharmaceutical preparations for delivery by various routes are formulated as shown in the following Tables. "Active ingredient" or "Active compound" as used in the Tables means one or more of the Compounds of Formula I.

| Composition for Oral Administration | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s.to 100 mL |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 38

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-$HT_{2A}$ receptor. Membranes were prepared from HEK 293 cell lines by the method described by Monsma et al., Molecular Pharmacology, Vol. 43 pp. 320–327 (1993), and from CHO-K1cell lines as described by Bonhaus et al., Br J Pharmacol. Jun; 115(4):622–8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-$HT_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [³H] LSD or [³H]Ketanserin (5 nM), competing ligand, and membrane were incubated in a shaking water bath for 75 min. at 37° C. (for 5-HT₆) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound[³H]LSD or [³H]Ketanserin were determined as radioactive counts per minute using Packard TopCount.

Displacement of [³H]LSD or [³H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-\text{Hill}(\log[\text{ligand}] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT₆ antagonists, selective 5-HT$_{2A}$ antagonists, or both. For example, the compound 8-Fluoro-4-piperazin-1-yl-10-(3-trifluoromethyl-benzyl)-10H-dibenzo[b,f][1,4]oxazepin-11-one exhibted a pKi of approximately 9.55 for 5-HT₆, and 6-Fluoro-10-phenethyl-4-piperazin-1-yl-10H-dibenzo[b,f][1,4]oxazepin-11-one, hydrochloride showed a pKi of approximately 8.88 for 5-HT$_{2A}$.

Example 39

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur et al., "A new one-trial test for neurobiological studies of memory in rats. 1: Behavioral data," *Behav. Brain Res.*, 1988, 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

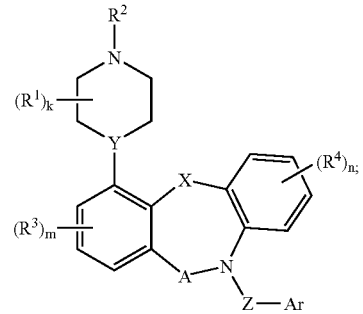

or a pharmaceutically accentable salt thereof, wherein
A is C(=O) or CH₂;
X is O—, S(O)$_q$—, or —NR⁸—;
Y is —N— or —CH—;
Z is —(CR⁶R⁷)$_r$—, or —S(O)$_t$—;
Ar is phenyl optionally substituted with halo, alkyl, haloalkyl, heteroalkyl, alkoxy, cyano, —S(O)$_q$—R$^c$, —C(=O)—NR$^c$R$^d$, —SO₂—NR$^c$R$^d$, —N(R$^c$)—C(=O)—R$^d$, or —C(=O)—R$^c$; or heteroaryl selected from pyridin-3-yl, 2-chlorothien-5-yl and indolyl-3-yl;
each R¹ is independently hydrogen or alkyl;
each of R², R⁶, R⁷ and R⁸ is independently hydrogen or alkyl;
each of R³ and R⁴ is independently halo, alkyl, haloalkyl, alkoxy, cyano, —S(O)$_s$—R$^c$, —C(=O)—NR$^c$R$^d$, —SO₂—NR$^c$R$^d$, —N(R$^c$)—C(=O)—R$^d$, or —C(=O)—R$^c$;
each of R$^c$ and R$^d$ is independently hydrogen or alkyl;
each of m and n is independently an integer from 0 to 3;
r is an integer from 1 to 3; and
each of k, q, s, and t is independently an integer from 0 to 2.

2. The compound of claim 1, wherein said compound of the formula II:

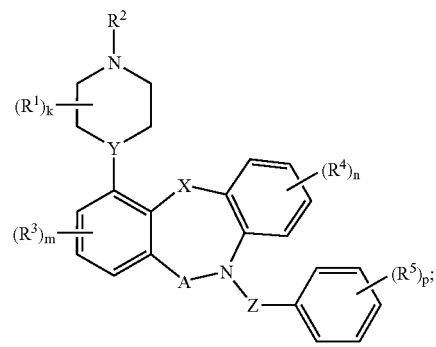

wherein
each R⁵ is independently halo, alkyl, haloalkyl, alkoxy, cyano, —S(O)$_s$—R$^c$, —C(=O)—NR$^c$R$^d$, —SO₂—NR$^c$R$^d$, N(R$^c$)C(=O) R$^d$, or —C(=O)—R$^c$;
each of R$^c$ and R$^d$ is independently hydrogen or alkyl; and
p is an integer from 0 to 3;
each is independently.

3. The compound according to claim 1, wherein A is C=O.

4. The compound according to claim 1, wherein A is CH$_2$—.

5. The compound according to claim 4, wherein Z is —S(O).

6. The compound according to claim 1, wherein each of R$^3$ and R$^4$, is independently alkyl, alkoxy, halo, hydroxyl, cyano, or haloalkyl.

7. The compound according to claim 6 wherein m is 0 or 1.

8. The compound according to claim 7, wherein R$^3$ is halo.

9. The compound according to claim 6, wherein n is 0 or 1.

10. The compound according to claim 9, wherein R$^4$ is halo or alkyl.

11. The compound according to claim 2, wherein p is 0 or 1.

12. The compound according to claim 11, wherein R$^5$ is halo, alkyl, alkoxy, haloalkyl, cyano, or hydroxyl.

13. The compound according to claim 1, wherein X is S(O)$_q$.

14. The compound according to claim 1, wherein X is —O—.

15. The compound according to claim 14, wherein Y is —CH—.

16. The compound according to claim 14, wherein Y is —N—.

17. The compound according to claim 1, wherein Z is —(CR$^6$R$^7$)$_T$.

18. The compound according to claim 17, wherein R$^6$ and R$^7$ are hydrogen.

19. The compound according to claim 1, wherein k is 0.

20. The compound according to claim 1, wherein R$^2$ is hydrogen or methyl.

21. The compound according to claim 1, wherein said compound is selected from the group consisting of:
- 10-Benzyl-4-piperazin-1-yl-10H-dibenzo[b,f][1,4]oxazepin-11-one;
- 10-(4-Fluoro-benzyl)-4-piperazin-1-yl-10H-dibenzo[b,f][1,4]oxazepin-11-one;
- 10-(3-Fluoro-benzyl)-4-piperazin-1-yl-10H-dibenzo[b,f][1,4]oxazepin-11-one;
- 10-(2-Fluoro-benzyl)-4-piperazin-1-yl-10H-dibenzo[b,f][1,4]oxazepin-11-one;
- 4-Piperazin-1-yl-10-(3-trifluoromethyl-benzyl)-10H-dibenzo[b,f][1,4]oxazepin-11-one;
- 3-(11-Oxo-4-piperazin-1-yl-11H-dibenzo[b,f][1,4]oxazepin-10-ylmethyl)-benzonitrile;
- 10-(3-Chloro-benzyl)-4-piperazin-1-yl-10H-dibenzo[b,f][1,4]oxazepin-11-one;
- 10-Benzyl-2-chloro-4-piperazin-1-yl-10H-dibenzo[b,f][1,4]oxazepin-11-one;
- 10-(3-Methyl-benzyl)-4-piperazin-1-yl-10H-dibenzo[b,f][1,4]oxazepin-11-one;
- 10-Phenethyl-4-piperazin-1-yl-10H-dibenzo[b,f][1,4]oxazepin-11-one;
- 10-(3-Methoxy-benzyl)-4-piperazin-1-yl-10H-dibenzo[b,f][1,4]oxazepin-11-one;
- 10-(4-Methanesulfonyl-benzyl)-4-piperazin-1-yl-10H-dibenzo[b,f][1,4]oxazepin-11-one;
- 10-Benzyl-4-piperazin-1-yl-5,10-dihydro-dibenzo[b,e][1,4]diazepin-11-one;
- 10-Benzyl-8-tert-butyl-4-piperazin-1-yl-10H-dibenzo[b,f][1,4]oxazepin-11-one;
- 10-Benzyl-7-fluoro-4-piperazin-1-yl-10H-dibenzo[b,f][1,4]oxazepin-11-one;
- 10-(3-Chloro-benzyl)-7-fluoro-4-piperazin-1-yl-10H-dibenzo[b,f][1,4]oxazepin-11-one;
- 7-Fluoro-10-phenethyl-4-piperazin-1-yl-10H-dibenzo[b,f][1,4]oxazepin-11-one;
- 10-(3-Phenyl-propyl)-4-piperazin-1-yl-10H-dibenzo[b,f][1,4]oxazepin-11-one;
- 10-Benzyl-8-ethanesulfonyl-4-piperazin-1-yl-10H-dibenzo[b,f][1,4]oxazepin-11-one;
- 10-Benzyl-4-piperazin-1-yl-10H-dibenzo[b,f][1,4]thiazepin-11-one;
- 10-Benzyl-8-fluoro-4-piperazin-1-yl-10H-dibenzo[b,f][1,4]oxazepin-11-one;
- 10-(5-Chloro-thiophen-2-ylmethyl)-4-piperazin-1-yl-10H-dibenzo[b,f][1,4]-oxazepin-11-one;
- 10-Benzyl-9-fluoro-4-piperazin-1-yl-10H-dibenzo[b,f][1,4]oxazepin-11-one;
- 10-Benzyl-6-fluoro-4-piperazin-1-yl-10H-dibenzo[b,f][1,4]oxazepin-11-one;
- 10-(3-Chloro-benzyl)-6-fluoro-4-piperazin-1-yl-10H-dibenzo[b,f][1,4]oxazepin-11-one;
- 6-Fluoro-10-phenethyl-4-piperazin-1-yl-10H-dibenzo[b,f][1,4]oxazepin-11-one;
- 10-(3-Chloro-benzyl)-8-fluoro-4-piperazin-1-yl-10H-dibenzo[b,f][1,4]oxazepin-11-one;
- 8-Fluoro-4-piperazin-1-yl-10-(3-trifluoromethyl-benzyl)-10H-dibenzo[b,f][1,4]oxazepin-11-one;
- 8-Fluoro-10-(4-fluoro-benzyl)-4-piperazin-1-yl-10H-dibenzo[b,f][1,4]oxazepin-11-one;
- 4-Piperazin-1-yl-10-pyridin-3-ylmethyl-10H-dibenzo[b,f][1,4]oxazepin-11-one;
- 10-(3-Hydroxy-benzyl)-4-piperazin-1-yl-10H-dibenzo[b,f][1,4]oxazepin-11-one;
- 10-Benzenesulfonyl-4-(4-methyl-piperazin-1-yl)-10,11-dihydro-dibenzo[b,f][1,4]-oxazepine;
- 8-Fluoro-10-(3-hydroxy-benzyl)-4-piperazin-1-yl-10H-dibenzo[b,f][1,4]oxazepin-11-one;
- 10-Benzyl-8-chloro-4-piperazin-1-yl-10H-dibenzo[b,f][1,4]oxazepin-11-one;
- 8-Chloro-10-(3-chloro-benzyl)-4-piperazin-1-yl-10H-dibenzo[b,f][1,4]oxazepin-11-one;
- 8-Chloro-4-piperazin-1-yl-10-(3-trifluoromethyl-benzyl)-10H-dibenzo[b,f][1,4]oxazepin-11-one;
- 10-(1H-Indol-3-ylmethyl)-4-piperazin-1-yl-10H-dibenzo[b,f][1,4]oxazepin-11-one; and
- 10-Benzyl-2-methyl-4-piperidin-4-yl-10H-dibenzo[b,f][1,4]oxazepin-11-one.

22. A pharmaceutical composition comprising a therapeutically effective amount of a compound of claim 1 and a pharmaceutically acceptable carrier.

23. A method for enhancing cognition in an Alzheimer's patient, said method comprising administering to said patient a therapeutically effective amount of a compound of claim 1.

24. A method for preparing a compound of the formula I;

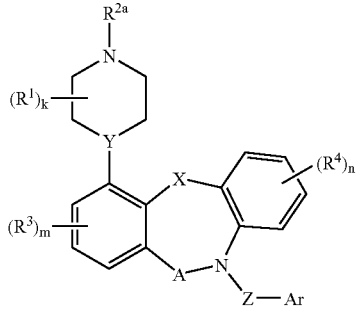

said method comprising reacting an amino compound of the formula:

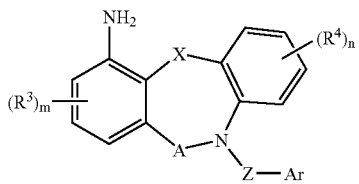

with an amino compound of the formula:

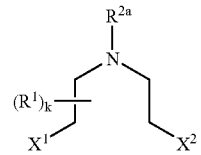

to produce the compound, of formula I,
wherein
each of m and n is independently an integer from 0 to 3;
Ar is optionally substituted aryl or optionally substituted heteroaryl;
A is C(=O) or CH$_2$;
X is —O—, —S(O)$_q$—, or —NR$^8$—;
Z is —CR$^6$R$^7$)$_r$—, or —S(O)$_t$—;
each R$^1$ is independently alkyl;
each of R$^6$, R$^7$, R$^8$ is independently hydrogen or alkyl;
each of R$^3$, R$^4$, and R$^5$ is independently halo, alkyl, haloalkyl, heteroalkyl, alkoxy, cyano, S(O)$_s$—R$^c$, C(=O)—NR$^c$R$^d$, —SO$_2$—NR$^c$R$^d$, —N(R$^c$)—C(=O)—R$^d$, or —C(=O)—R$^c$;
each of R$^c$ and R$^d$ is independently hydrogen or alkyl;
each of m, n, and p is independently an integer from 0 to 3;
r is an integer from 1 to 3; and
each of k, q, s, and t is independently an integer from 0 to 2.
R$^{2a}$ is hydrogen, alkyl, or an amino-protecting group; and
each of X$^1$ and X$^2$ is independently a leaving group.

* * * * *